US011646099B2

(12) United States Patent
Staudt et al.

(10) Patent No.: US 11,646,099 B2
(45) Date of Patent: May 9, 2023

(54) METHOD FOR DETERMINING LYMPHOMA TYPE AND PROVIDING TREATMENT

(71) Applicants: The United States of America, as represented by the Secretary, Department of Health and Human Services, Bethesda, MD (US); British Columbia Cancer Agency Branch, Vancouver (CA); Mayo Foundation for Medical Education and Research, Rochester, MN (US); Julius-Maximilians-University of Würzburg, Würzburg (DE); Board of Regents of the University of Nebraska, Lincoln, NE (US); Oslo University Hospital HF, Oslo (NO); Hospital Clinic de Barcelona, Barcelona (ES); Universitat de Barcelona, Barcelona (ES); Institut D'Investigacions Biomèdiques August Pi I Sunyer (IDIBAPS), Barcelona (ES); Robert Bosch Gesellschaft fuer medizinische Forschung mbH, Stuttgart (DE); Oregon Health & Science University, Portland, OR (US); City of Hope, Duarte, CA (US); The Cleveland Clinic Foundation, Cleveland, OH (US)

(72) Inventors: Louis M. Staudt, Bethesda, MD (US); Christian Steidl, North Vancouver (CA); Anja Mottok, Ulm (DE); George W. Wright, Rockville, MD (US); David William Scott, Vancouver (CA); Lisa M. Rimsza, Scottsdale, AZ (US); Andreas Rosenwald, Würzburg (DE); Randy Gascoyne, North Vancouver (CA); Timothy Greiner, Council Bluffs, IA (US); Dennis Weisenburger, Glendora, CA (US); Erlend B. Smeland, Oslo (NO); Jan Delabie, Toronto (CA); Elias Campo Guerri, Barcelona (ES); German Ott, Bitighein-Bissingen (DE); Rita Braziel, West Linn, OR (US); Elaine S. Jaffe, Great Falls, VA (US); Kai Fu, Omaha, NE (US); Wing C. Chan, Pasadena, CA (US); Joo Song, Duarte, CA (US); James R. Cook, Shaker Heights, OH (US)

(73) Assignees: The United States of America, as represented by the Secretary, Department of Health and Human Services, Bethesda, MD (US); British Columbia Cancer Agency, Vancouver (CA); Mayo Foundation for Medical Education and Research, Rochester, MN (US); Julius-Maximilians-University of Würzburg, Würuzburg (DE); Boatd of Regents of the University of Nebraska, Lincoln, NE (US); Oslo University Hospital HF, Oslo (NO); Hospital Clinic de Barcelona, Barcelona (ES); Universitat de Barceloa, Barcelona (ES); Institut D'Investigacions Biomédiques Pi I Sunyer (IDIBAPS), Barcelona (ES); Robert Bosch Gesellschaft feuer medizinische Forshung mbH, Stuttgart (DE); Oregon Health & Science University, Portland, OR (US); City of Hope, Duarte, CA (US); The Cleveland Clinic Foundation, Cleveland, OH (US)

( * ) Notice: Subject to any disclaimer, the term of this patent is extended or adjusted under 35 U.S.C. 154(b) by 711 days.

(21) Appl. No.: 16/713,528

(22) Filed: Dec. 13, 2019

(65) Prior Publication Data

US 2020/0105364 A1   Apr. 2, 2020

Related U.S. Application Data

(63) Continuation-in-part of application No. PCT/US2018/036084, filed on Jun. 5, 2018.

(Continued)

(51) Int. Cl.
*G01N 33/48*     (2006.01)
*G16B 5/00*     (2019.01)
(Continued)

(52) U.S. Cl.
CPC ............. *G16B 5/00* (2019.02); *C12Q 1/6886* (2013.01); *G16B 25/10* (2019.02); *C12Q 2600/112* (2013.01); *C12Q 2600/158* (2013.01)

(58) Field of Classification Search
None
See application file for complete search history.

(56) References Cited

U.S. PATENT DOCUMENTS

| | | |
|---|---|---|
| 2011/0152115 A1 | 6/2011 | Staudt et al. |
| 2013/0195843 A1 | 8/2013 | Morin et al. |

(Continued)

FOREIGN PATENT DOCUMENTS

| | | |
|---|---|---|
| WO | WO 2005/024043 A2 | 3/2005 |
| WO | WO 2008/013910 A2 | 1/2008 |

(Continued)

OTHER PUBLICATIONS

Alizadeh et al., "Distinct Types of Diffuse Large B-cell Lymphoma Identified by Gene Expression Profiing," *Nature* 403: 503-511 (2000).

(Continued)

*Primary Examiner* — Anna Skibinsky
(74) *Attorney, Agent, or Firm* — Leydig, Voit & Mayer, Ltd.

(57) ABSTRACT

In embodiments of the invention, the invention provides a method for distinguishing between lymphoma types based (Continued)

on gene expression measurements. In embodiments, the invention distinguishes between PMBCL and DLBCL based on gene expression signatures, and can further distinguish between DLBCL subtypes. In embodiments of the invention, the distinctions are used in methods of treatment.

7 Claims, 5 Drawing Sheets

Specification includes a Sequence Listing.

Related U.S. Application Data

(60) Provisional application No. 62/519,728, filed on Jun. 14, 2017.

(51) Int. Cl.
    *G16B 25/10*    (2019.01)
    *C12Q 1/6886*    (2018.01)

(56) References Cited

U.S. PATENT DOCUMENTS

| | | |
|---|---|---|
| 2015/0167088 A1 | 6/2015 | Staudt et al. |
| 2016/0283653 A1 | 9/2016 | Staudt et al. |
| 2017/0016074 A1 | 1/2017 | Jardin et al. |

FOREIGN PATENT DOCUMENTS

| | | |
|---|---|---|
| WO | WO 2015/069790 A9 | 5/2015 |
| WO | WO 2017/059108 A1 | 4/2017 |

OTHER PUBLICATIONS

Dunleavy et al., "Dose-Adjusted EPOCH-Rituximab Therapy in Primary Mediastinal B-Cell Lymphoma," *N Engl J Med.* 368(15): 1408-1416 (2003), "Author Manuscript" as published in PubMed, with Supplementary Appendix.
European Patent Office, Written Opinion of the International Searching Authority, European Patent Office PCT/US2018/036084, dated Sep. 11, 2018, 10 pages.
European Patent Office, International Search Report, European Patent Office PCT/US2018/036084, dated Sep. 11, 2018, 8 pages.
Fortina et al., "Digital mRNA Profiling," *Nature Biotechnology*, 26(3): 293-294 (Mar. 2008).
Geiss et al., "Direct Multiplexed Measurement of Gene Expression with Color-coded Probe Pairs," *Nature Biotechnology* 26(3): 317-325 (Mar. 2008).
International Bureau of WIPO, International Preliminary Report on Patentability, PCT/US2018/036084 dated Dec. 26, 2019, 9 pages.
Lenz et al., "Stromal Gene Signatures in Large-Cell Lymphomas," *N Engl J Med.* 359(22): 2313-2323 (Nov. 27, 2008).
Mottok et al., "Integrative Genomic Analysis Identifies Key Pathogenic Mechanisms in Primary Mediastinal Large B-cell Lymphoma," *Blood* 134(10): 802-813 (ePub Jul. 10, 2019).
Mottok et al., "Molecular Classification of Primary Mediastinal Large B-cell Lymphoma Using Routinely Available Tissue Specimens," *Blood* 134(10): 2401-2405 (Nov. 29, 2018) published online Sep. 26, 2018.
Mottok et al., "Molecular Classification of Primary Mediastinal Large B-cell Lymphoma Using Formalin-fixed, Paraffin-embedded Tissue Specimens—An LLMPP Project," Abstract 47, *Hematol Oncol*, 35: 59-60 (Jun. 7, 2017).
Rimsza et al., "Accurate Classification of Diffuse Large B Cell Lymphoma into Germinal Center and Activated B Cell Subtypes Using a Nuclease Protection Assay on Formalin Fixed Paraffin Embedded Tissues," *Clin Cancer Res* 17(11): 3727-3732 (Jun. 1, 2011) "Author Manuscript" as published in PubMed.
Rimsza, "PMBL: Flying Under the Immune Radar," *Blood* 134(10): 788-789 (Sep. 5, 2019).
Rosenwald et al., "Molecular Diagnosis of Primary Mediastinal B Cell Lymphoma Identifies a Clinically Favorable Subgroup of Diffuse Large B Cell Lymphoma Related to Hodgkin Lymphoma," *J Experimental Medicine* 198(6): 851-862 (Sep. 15, 2003).
Rosenwald et al., "The Use of Molecular Profiling to Predict Survival After Chemotherapy for Diffuse Large B-Cell Lymphoma," *New England of Journal of Medicine*, 346(25): 1937-1947 (Jun. 20, 2002).
Scott et al., "Determining Cell-of-Origin Subtypes of Diffuse Large B-cell Lymphoma Using Gene Expression in Formalin-fixed Paraffin-embedded Tissue," *Blood*, 123(8): 1214-1217 (Feb. 20, 2014).
Scott et al., "Prognostic Significance of Diffuse Large B-Cell Lymphoma Cell of Origin Determined by Digital Gene Expression in Formalin-Fixed Paraffin-Embedded Tissue Biopsies," Journal of Clinical Oncology 33(26): 2848-2856 (Sep. 10, 2015).
Veldman-Jones et al., "Reproducible, Quantitative, and Flexible Molecular Subtyping of Clinical DLBCL Samples Using the NanoString nCounter System," *Clinical Cancer Research*, 21(10): 2367-2378 (2015) epublished Oct. 9, 2014.
Wright et al., "A Gene Expression-based Method to Diagnose Clinically Distinct Subgroups of Diffuse Large B Cell Lymphoma," *PNAS* 100(17): 9991-9996 (Aug. 19, 2003).

SEQUENCE LISTING

```
<160> NUMBER OF SEQ ID NOS: 58

<210> SEQ ID NO 1
<211> LENGTH: 100
<212> TYPE: DNA
<213> ORGANISM: Artificial Sequence
<220> FEATURE:
<223> OTHER INFORMATION: synthetic

<400> SEQUENCE: 1
ggacacgtag gcggtaccac taaggttttg gtaatgagcc attcaaaccg acagcagtgt       60
gaaggtgtgt caaggtgtat attctcgtgg ctcggcattc                            100

<210> SEQ ID NO 2
<211> LENGTH: 100
<212> TYPE: DNA
<213> ORGANISM: Artificial Sequence
<220> FEATURE:
<223> OTHER INFORMATION: synthetic

<400> SEQUENCE: 2
ggtggtcttg aactggcttt agcctgtgat atacgagtag cagcttcctc tgcaaaaatg       60
ggcctggttg aaacaaaatt ggcgattatt cctggtggag                            100

<210> SEQ ID NO 3
<211> LENGTH: 100
<212> TYPE: DNA
<213> ORGANISM: Artificial Sequence
<220> FEATURE:
<223> OTHER INFORMATION: synthetic

<400> SEQUENCE: 3
ggcaaatgaa atggaagggg aaggaaaaca gaatggatca ggcatggaga ccaaacacag       60
cccactagag gttggcagtg agagttctga agaccagtat                            100
```

<210> SEQ ID NO 4
<211> LENGTH: 100
<212> TYPE: DNA
<213> ORGANISM: Artificial Sequence
<220> FEATURE:
<223> OTHER INFORMATION: synthetic

<400> SEQUENCE: 4
ctgctgttat gcagagccat ttcctctaga atttggataa taaagatgct tattgtctct    60
cccttctcca gttctgggaa tttacaggca caatacactt                         100

<210> SEQ ID NO 5
<211> LENGTH: 100
<212> TYPE: DNA
<213> ORGANISM: Artificial Sequence
<220> FEATURE:
<223> OTHER INFORMATION: synthetic

<400> SEQUENCE: 5
tgctctcctt gggatgatgg ctggctagtc agccttgcat gtattccttg gctgaatggg    60
agagtgcccc atgttctgca agactacttg gtattcttgt                         100

<210> SEQ ID NO 6
<211> LENGTH: 100
<212> TYPE: DNA
<213> ORGANISM: Artificial Sequence
<220> FEATURE:
<223> OTHER INFORMATION: synthetic

<400> SEQUENCE: 6
ttgaaaatcg gcccaagaag gagcaggttc tggaactgga gcgggagaat gaaatgctga    60
agaccaaaaa ccaggagctg cagtccatca tccaggccgg                         100

<210> SEQ ID NO 7
<211> LENGTH: 100
<212> TYPE: DNA
<213> ORGANISM: Artificial Sequence
<220> FEATURE:
<223> OTHER INFORMATION: synthetic

<400> SEQUENCE: 7
aaacactttc agagttccc tgcaacccgt gcttatgcag atagttacta ttatgaagat     60
ggaggaatga agccaagagt gatgaaagaa gctgtatcta                         100

<210> SEQ ID NO 8
<211> LENGTH: 100
<212> TYPE: DNA
<213> ORGANISM: Artificial Sequence
<220> FEATURE:
<223> OTHER INFORMATION: synthetic

<400> SEQUENCE: 8
gcctggagta cttcaaggga gccattcccc ttagaaagct gaagacgtgg taccagacat    60
ctgaggactg ctccagggat gccatcgttt ttgtaactgt                         100

<210> SEQ ID NO 9
<211> LENGTH: 100
<212> TYPE: DNA
<213> ORGANISM: Artificial Sequence
<220> FEATURE:
<223> OTHER INFORMATION: synthetic

<400> SEQUENCE: 9

```
atgcctgagg ggatcaggct tttctactcc aggcaaacct gccccatctt gtcgctttta    60
ggacctccca caacctggtt ccccacacat ccatagttct                         100
```

<210> SEQ ID NO 10
<211> LENGTH: 100
<212> TYPE: DNA
<213> ORGANISM: Artificial Sequence
<220> FEATURE:
<223> OTHER INFORMATION: synthetic

<400> SEQUENCE: 10

```
ccatgtctta gggcttcctg taggtaacta tgtccagctc ttggcaaaaa tcgataatga    60
attggtggtc agggcttaca cccctgtctc cagtgatgat                         100
```

<210> SEQ ID NO 11
<211> LENGTH: 100
<212> TYPE: DNA
<213> ORGANISM: Artificial Sequence
<220> FEATURE:
<223> OTHER INFORMATION: synthetic

<400> SEQUENCE: 11

```
tttcttccat gttttagaaa atgaggcctg tttggggaag gtaccctggt gatgttttg     60 ctagacatta gctgtagctg acagcataag gagagtcgca                         100
```

<210> SEQ ID NO 12
<211> LENGTH: 100
<212> TYPE: DNA
<213> ORGANISM: Artificial Sequence
<220> FEATURE:
<223> OTHER INFORMATION: synthetic

<400> SEQUENCE: 12

```
acagctacat gtggtggctc agcattggcg ctctcatagg cctgtccgta gcagcagtgg    60
ttcttctcgc cttcattgtt accgcctgtg tgctctgcta                         100
```

<210> SEQ ID NO 13
<211> LENGTH: 100
<212> TYPE: DNA
<213> ORGANISM: Artificial Sequence
<220> FEATURE:
<223> OTHER INFORMATION: synthetic

<400> SEQUENCE: 13

```
ccctgccctc ttgtctgcca cggggcgagt ctggcacctc tttcttctga cctcagacgg    60
ctctgagcct tatttctctg gaagcggcta agggacggtt                         100
```

<210> SEQ ID NO 14
<211> LENGTH: 100
<212> TYPE: DNA
<213> ORGANISM: Artificial Sequence
<220> FEATURE:
<223> OTHER INFORMATION: synthetic

<400> SEQUENCE: 14

```
cagattttac aggctgaatt attggcagta tatggagcag acccaggcac acaggattct    60
agtgggaaaa ctcccgttga ttatgcaagg caaggagggc                         100
```

<210> SEQ ID NO 15
<211> LENGTH: 100
<212> TYPE: DNA
<213> ORGANISM: Artificial Sequence
<220> FEATURE:
<223> OTHER INFORMATION: synthetic

<400> SEQUENCE: 15
actgattata cctctagtat agatgtatgg tctgctggct gtgtgttggc tgagctgtta        60
ctaggacaac caatatttcc aggggatagt ggtgtggatc                              100

<210> SEQ ID NO 16
<211> LENGTH: 100
<212> TYPE: DNA
<213> ORGANISM: Artificial Sequence
<220> FEATURE:
<223> OTHER INFORMATION: synthetic

<400> SEQUENCE: 16
tggaagacaa agtgcgttcc ttaaagacag acattgagga gagcaaatac cgacagcgcc        60
acctgaaggt ggagttgaag agcttcctgg aggtgctgga                              100

<210> SEQ ID NO 17
<211> LENGTH: 100
<212> TYPE: DNA
<213> ORGANISM: Artificial Sequence
<220> FEATURE:
<223> OTHER INFORMATION: synthetic

<400> SEQUENCE: 17
gcttgggaga accctctccc ttctctgaga aagaaagatg tcgaatgggt attccacaga        60
cgagaatttc cgctatctca tctcgtgctt cagggccagg                              100

<210> SEQ ID NO 18
<211> LENGTH: 100
<212> TYPE: DNA
<213> ORGANISM: Artificial Sequence
<220> FEATURE:
<223> OTHER INFORMATION: synthetic

<400> SEQUENCE: 18
gtccaaattc ttgggtggtg acatggaaca cacccatttg gtgaaaggct tggattttgc        60
tctgcttcaa aaggtacgag ctgagattgc cagcaaagag                              100

<210> SEQ ID NO 19
<211> LENGTH: 100
<212> TYPE: DNA
<213> ORGANISM: Artificial Sequence
<220> FEATURE:
<223> OTHER INFORMATION: synthetic

<400> SEQUENCE: 19
tctgcactgg aagaagtacg acatctatga gaagcaaacc aaggaggaaa ccgactctgt        60
agtgctgata gaaaacctga agaaagcctc tcagtgatgg                              100

<210> SEQ ID NO 20
<211> LENGTH: 100
<212> TYPE: DNA
<213> ORGANISM: Artificial Sequence
<220> FEATURE:
<223> OTHER INFORMATION: synthetic

<400> SEQUENCE: 20
gggcactgtt taaaggaaag ttccgagaag gcatcgacaa gccggaccct cccacctgga        60
agacgcgcct gcggtgcgct ttgaacaaga gcaatgactt                              100

<210> SEQ ID NO 21
<211> LENGTH: 100
<212> TYPE: DNA
<213> ORGANISM: Artificial Sequence
<220> FEATURE:
<223> OTHER INFORMATION: synthetic

<400> SEQUENCE: 21
ggcaaaacat cagtgtctgt gggtagttgg aatcttcagt tcctgtgagc gtcggcgtct    60
tctgggcctg tggagtttct tggacagggg ccgcgggct                          100

<210> SEQ ID NO 22
<211> LENGTH: 100
<212> TYPE: DNA
<213> ORGANISM: Artificial Sequence
<220> FEATURE:
<223> OTHER INFORMATION: synthetic

<400> SEQUENCE: 22
gtggcctcct ggcatcattt gttattgcct ctgaaacaag ccttactgcc tggagggctt    60
agattcctgc ttctccaatg tagtgtgggt atcttgtagg                          100

<210> SEQ ID NO 23
<211> LENGTH: 100
<212> TYPE: DNA
<213> ORGANISM: Artificial Sequence
<220> FEATURE:
<223> OTHER INFORMATION: synthetic

<400> SEQUENCE: 23
aactacatcc tgaactcgac gtcctgaggt ataatacaac agagcacttt ttgaggcaat    60
tgaaaaacca acctacactc ttcggtgctt agagagatct                          100

<210> SEQ ID NO 24
<211> LENGTH: 100
<212> TYPE: DNA
<213> ORGANISM: Artificial Sequence
<220> FEATURE:
<223> OTHER INFORMATION: synthetic

<400> SEQUENCE: 24
aaggcaagtc tcaggaaccc atgcaggtac atcgcttgca cctgttttta gcttatttaa    60
tgacgggctt ttgggaagag ctgcccgcat actgagagac                          100

<210> SEQ ID NO 25
<211> LENGTH: 100
<212> TYPE: DNA
<213> ORGANISM: Artificial Sequence
<220> FEATURE:
<223> OTHER INFORMATION: synthetic

<400> SEQUENCE: 25
gccttcgcgt ccgggttggg agcttgctgt gtctaacctc caactgctgt gctgtctgct    60
agggtcacct cctgtttgtg aaaggggacc ttcttgttcg                          100

<210> SEQ ID NO 26
<211> LENGTH: 100
<212> TYPE: DNA
<213> ORGANISM: Artificial Sequence
<220> FEATURE:
<223> OTHER INFORMATION: synthetic

<400> SEQUENCE: 26

```
tggaagccat caacaatttg cccagtaaca tgccactgcc ttcagcttct cctcttcacc    60
aacttgacct gaaaccttct ttgcccttgc agaacagtgg                         100

<210> SEQ ID NO 27
<211> LENGTH: 100
<212> TYPE: DNA
<213> ORGANISM: Artificial Sequence
<220> FEATURE:
<223> OTHER INFORMATION: synthetic

<400> SEQUENCE: 27
ggattgtagg tgcaagctgt ccagagaaaa gagtccttgt tccagcccta ttctgccact    60
cctgacaggg tgaccttggg tatttgcaat attcctttgg                         100

<210> SEQ ID NO 28
<211> LENGTH: 100
<212> TYPE: DNA
<213> ORGANISM: Artificial Sequence
<220> FEATURE:
<223> OTHER INFORMATION: synthetic

<400> SEQUENCE: 28
ttctcttacc cagagatgcc catgagctga cattttactc atccctctgc ctccaagaag    60
gcctgtatta tacgtgtcct cctgggggtt ggagatgatc                         100

<210> SEQ ID NO 29
<211> LENGTH: 100
<212> TYPE: DNA
<213> ORGANISM: Artificial Sequence
<220> FEATURE:
<223> OTHER INFORMATION: synthetic

<400> SEQUENCE: 29
ccactttgga gttgtctacc acggagaata catagaccag gcccagaatc gaatccaatg    60
tgccatcaag tcactaagtc gcatcacaga gatgcagcag                         100

<210> SEQ ID NO 30
<211> LENGTH: 100
<212> TYPE: DNA
<213> ORGANISM: Artificial Sequence
<220> FEATURE:
<223> OTHER INFORMATION: synthetic

<400> SEQUENCE: 30
ggcaaacgct gtgttatcct ctttgcagac catcccagaa tttgcagaga ctctagaact    60
tattgaatct gatcctgtag catggagtga cgttaccagt                         100

<210> SEQ ID NO 31
<211> LENGTH: 100
<212> TYPE: DNA
<213> ORGANISM: Artificial Sequence
<220> FEATURE:
<223> OTHER INFORMATION: synthetic

<400> SEQUENCE: 31
ctctcctctc ctccttgtct ggctctgttg acaaaccggg catgtttggc agtaaattgg    60
caccgtgtca cactgtttcc tgggattcaa gtatgcaacc                         100

<210> SEQ ID NO 32
<211> LENGTH: 100
<212> TYPE: DNA
```

<210> SEQ ID NO 33
<211> LENGTH: 100
<212> TYPE: DNA
<213> ORGANISM: Artificial Sequence
<220> FEATURE:
<223> OTHER INFORMATION: synthetic

<400> SEQUENCE: 32
cctttctttc tcctcgccgg cccgagagca ggaacacgat aacgaaggag gcccaacttc    60
attcaataag gagcctgacg gatttatccc agacggtaga                          100

<210> SEQ ID NO 33
<211> LENGTH: 100
<212> TYPE: DNA
<213> ORGANISM: Artificial Sequence
<220> FEATURE:
<223> OTHER INFORMATION: synthetic

<400> SEQUENCE: 33
ctgagaccat atccttaaat gtaaaaggcc ctggactaca gaggatggtg cttgttgact    60
taccaggtgt gattaatact gtgacatcag gcatggctcc                          100

<210> SEQ ID NO 34
<211> LENGTH: 100
<212> TYPE: DNA
<213> ORGANISM: Artificial Sequence
<220> FEATURE:
<223> OTHER INFORMATION: synthetic

<400> SEQUENCE: 34
aggaaaataa acactcacat cctaaaggtt ccagaaacag atgaggtaga gctcacctgc    60
caggctacag gttatcctct ggcagaagta tcctggccaa                          100

<210> SEQ ID NO 35
<211> LENGTH: 100
<212> TYPE: DNA
<213> ORGANISM: Artificial Sequence
<220> FEATURE:
<223> OTHER INFORMATION: synthetic

<400> SEQUENCE: 35
ctgtctgtgt cccgacacat aatctctgtc tcttggacct gccaccatca ctttctgggt    60
caggattgga attgggatgg aatgggacag ttgtctataa                          100

<210> SEQ ID NO 36
<211> LENGTH: 100
<212> TYPE: DNA
<213> ORGANISM: Artificial Sequence
<220> FEATURE:
<223> OTHER INFORMATION: synthetic

<400> SEQUENCE: 36
gccatccagc actgccattc ccgtggagtt gtccatcgtg acatcaagga tgagaacatc    60
ctgatagacc tacgccgtgg ctgtgccaaa ctcattgatt                          100

<210> SEQ ID NO 37
<211> LENGTH: 100
<212> TYPE: DNA
<213> ORGANISM: Artificial Sequence
<220> FEATURE:
<223> OTHER INFORMATION: synthetic

<400> SEQUENCE: 37
gcatggggaa gtttgtcccg ctggctggaa gcctggcagt gacacgatta agcccaacgt    60
ggatgacagc aaggaatatt tctccaaaca caattaggct                          100

<210> SEQ ID NO 38
<211> LENGTH: 100
<212> TYPE: DNA
<213> ORGANISM: Artificial Sequence
<220> FEATURE:
<223> OTHER INFORMATION: synthetic

<400> SEQUENCE: 38
gcatttggag tcctgctgta tgaaatgttg gctgggcagg cacccttga aggggaggat    60 gaagatgaac tcttccaatc catcatggaa cacaacgtag                         100

<210> SEQ ID NO 39
<211> LENGTH: 100
<212> TYPE: DNA
<213> ORGANISM: Artificial Sequence
<220> FEATURE:
<223> OTHER INFORMATION: synthetic

<400> SEQUENCE: 39
ttcattgttc cagcttctcg cttcaagctc ctgaagggag ctgagcacat aacgacttac    60
acgttcaata ctcacaaagc ccagcatacc ttctgtaaga                         100

<210> SEQ ID NO 40
<211> LENGTH: 100
<212> TYPE: DNA
<213> ORGANISM: Artificial Sequence
<220> FEATURE:
<223> OTHER INFORMATION: synthetic

<400> SEQUENCE: 40
ctgacatttc aagctgaccc tgtgatctct gccctgtctt cgggcgacag gagccagaaa    60
atcagggaca tggctgatgg ctgcggatgc tggaaccttg                         100

<210> SEQ ID NO 41
<211> LENGTH: 100
<212> TYPE: DNA
<213> ORGANISM: Artificial Sequence
<220> FEATURE:
<223> OTHER INFORMATION: synthetic

<400> SEQUENCE: 41
tagggcagct cagtccctgg cctcttagca ccacattcct gtttttcagc ttatttgaag    60
tcctgcctca ttctcactgg agcctcagtc tctcctgctt                         100

<210> SEQ ID NO 42
<211> LENGTH: 100
<212> TYPE: DNA
<213> ORGANISM: Artificial Sequence
<220> FEATURE:
<223> OTHER INFORMATION: synthetic

<400> SEQUENCE: 42
cctgtgttcc caagagaatt acattattga caaaagactc caagacgagg atgccagtag    60
tacccagcag aggcgccaga tatttagagt taataaagat                         100

<210> SEQ ID NO 43
<211> LENGTH: 100
<212> TYPE: DNA
<213> ORGANISM: Artificial Sequence
<220> FEATURE:
<223> OTHER INFORMATION: synthetic -continued

<400> SEQUENCE: 43
catttgaatt gtctcctgac tactgtccag taaggaggcc cattgtcact tagaaaagac    60
acctggaacc catgtgcatt tctgcatctc ctggattagc    100

<210> SEQ ID NO 44
<211> LENGTH: 100
<212> TYPE: DNA
<213> ORGANISM: Artificial Sequence
<220> FEATURE:
<223> OTHER INFORMATION: synthetic

<400> SEQUENCE: 44
tggtgaatca tttgaactga agattgtgcg acggggaatg cctcccggag gaggaggcga    60
agtggttttc tcatgtcctg tgaggaaggt cttgaagccc    100

<210> SEQ ID NO 45
<211> LENGTH: 100
<212> TYPE: DNA
<213> ORGANISM: Artificial Sequence
<220> FEATURE:
<223> OTHER INFORMATION: synthetic

<400> SEQUENCE: 45
ctgcggcaag acctcgctgc tcatggtgta cagccagggc tccttcccg agcactacgc    60 cccatcggtg ttcgagaagt acacggccag cgtgaccgtt    100

<210> SEQ ID NO 46
<211> LENGTH: 100
<212> TYPE: DNA
<213> ORGANISM: Artificial Sequence
<220> FEATURE:
<223> OTHER INFORMATION: synthetic

<400> SEQUENCE: 46
tcccgccagg tggcctcggc cttcatcgtc atcctctgtt gcgccattgt ggtggaaaac    60
cttctggtgc tcattgcggt ggcccgaaac agcaagttcc    100

<210> SEQ ID NO 47
<211> LENGTH: 100
<212> TYPE: DNA
<213> ORGANISM: Artificial Sequence
<220> FEATURE:
<223> OTHER INFORMATION: synthetic

<400> SEQUENCE: 47
ccactaaatc ctaggtggga aatggcctgt taactgatgg cacattgcta atgcacaaga    60
aataacaaac cacatccctc tttctgttct gagggtgcat    100

<210> SEQ ID NO 48
<211> LENGTH: 100
<212> TYPE: DNA
<213> ORGANISM: Artificial Sequence
<220> FEATURE:
<223> OTHER INFORMATION: synthetic

<400> SEQUENCE: 48
gtgtctcttg atccatccga agcaggccct ccacgttatc taggagatcg ctacaagttt    60
tatctggaga atctcaccct ggggatacgg gaaagcagga    100

<210> SEQ ID NO 49
<211> LENGTH: 100

<212> TYPE: DNA
<213> ORGANISM: Artificial Sequence
<220> FEATURE:
<223> OTHER INFORMATION: synthetic

<400> SEQUENCE: 49
tcatttgtat gtaggaccag gagtatctcc tcaggtgacc agttttgggg acccgtatgt    60
ggcaaattct aagctgccat attgaacatc atcccactgg                          100

<210> SEQ ID NO 50
<211> LENGTH: 100
<212> TYPE: DNA
<213> ORGANISM: Artificial Sequence
<220> FEATURE:
<223> OTHER INFORMATION: synthetic

<400> SEQUENCE: 50
tttaatccaa gatacagaac ctgtgatgct ttcacctata ctggctgtgg agggaatgac    60
aataactttg ttagcaggga ggattgcaaa cgtgcatgtg                          100

<210> SEQ ID NO 51
<211> LENGTH: 100
<212> TYPE: DNA
<213> ORGANISM: Artificial Sequence
<220> FEATURE:
<223> OTHER INFORMATION: synthetic

<400> SEQUENCE: 51
agatgctcaa ggagaacaag gtgttgaaga cactgaatgt ggaatccaac ttcatttctg    60
gagctgggat tctgcgcctg gtagaagccc tcccatacaa                          100

<210> SEQ ID NO 52
<211> LENGTH: 100
<212> TYPE: DNA
<213> ORGANISM: Artificial Sequence
<220> FEATURE:
<223> OTHER INFORMATION: synthetic

<400> SEQUENCE: 52
tgcaaaacca tttgcaacca tcagagccag cgcacctgtg cagccttctg caggtcactc    60
agctgccgca aggagcaagg caagttctat gaccatctcc                          100

<210> SEQ ID NO 53
<211> LENGTH: 100
<212> TYPE: DNA
<213> ORGANISM: Artificial Sequence
<220> FEATURE:
<223> OTHER INFORMATION: synthetic

<400> SEQUENCE: 53
cgagtgatgg gtctaggccc tgaaactgat gtcctagcaa taacctcttg atccctactc    60
accgagtgtt gagcccaagg ggggatttgt agaacaagcc                          100

<210> SEQ ID NO 54
<211> LENGTH: 100
<212> TYPE: DNA
<213> ORGANISM: Artificial Sequence
<220> FEATURE:
<223> OTHER INFORMATION: synthetic

<400> SEQUENCE: 54
gtggaggccg aggacatttt cctgaagggc aggggttggc aacttttcaa catggagtgc    60
caaactgcta acccgtcttc tagtgtgtga aatagggac                          100

<210> SEQ ID NO 55
<211> LENGTH: 100
<212> TYPE: DNA
<213> ORGANISM: Artificial Sequence
<220> FEATURE:
<223> OTHER INFORMATION: synthetic

<400> SEQUENCE: 55
catcgcgacg gccaaaagga gcggcgcggt cttcgtggtg ttcgtggcag gtgatgatga     60
acagtctaca cagatggctg caagttggga agatgataaa                          100

<210> SEQ ID NO 56
<211> LENGTH: 100
<212> TYPE: DNA
<213> ORGANISM: Artificial Sequence
<220> FEATURE:
<223> OTHER INFORMATION: synthetic

<400> SEQUENCE: 56
acagacaaga gtgggcgaca gtggaagctg aagtccttcc agaccaggga caaccagggc     60
attctctatg aagctgcacc cacctccacc ctcacctgtg                          100

<210> SEQ ID NO 57
<211> LENGTH: 100
<212> TYPE: DNA
<213> ORGANISM: Artificial Sequence
<220> FEATURE:
<223> OTHER INFORMATION: synthetic

<400> SEQUENCE: 57
cctctggact gaaccccaca tctgcacctc aacatctgc ttcagcggtc cctgtttctc      60
ctgttccaca gtcgccaata cctcccttac ttcaggaccc                          100

<210> SEQ ID NO 58
<211> LENGTH: 100
<212> TYPE: DNA
<213> ORGANISM: Artificial Sequence
<220> FEATURE:
<223> OTHER INFORMATION: synthetic

<400> SEQUENCE: 58
ctacctcttc aattggaatg gctttggggc cacaagtgac cgctttgccc tgagagctga     60
atctatcgac tgcatggttc cagtcaccga gagtctgctg                          100

METHOD FOR DETERMINING LYMPHOMA TYPE AND PROVIDING TREATMENT

CROSS-REFERENCE TO RELATED APPLICATIONS

This patent application is a continuation-in-part of International Patent Application No. PCT/US2018/036084, filed Jun. 5, 2018, which claims the benefit of U.S. Provisional Patent Application No. 62/519,728, filed Jun. 14, 2017, each of which is incorporated by reference herein in its entirety.

STATEMENT REGARDING FEDERALLY SPONSORED RESEARCH AND DEVELOPMENT

This invention was made with Government support under Grant Number U01CA157581 awarded by the Strategic Partnering to Evaluate Cancer Signatures (SPECS II). This invention was made with government support under Grant Number CA157581 awarded by the National Institutes of Health. This invention was made with Government support under project number ZIA BC011006-05 by the National Institutes of Health, National Cancer Institute. The Government has certain rights in this invention.

INCORPORATION-BY-REFERENCE OF MATERIAL SUBMITTED ELECTRONICALLY

Incorporated by reference in its entirety herein is a computer-readable nucleotide/amino acid sequence listing submitted concurrently herewith and identified as follows: one 16,045 Byte ASCII (Text) file named "746801_ST25.txt" dated Dec. 12, 2019.

BACKGROUND OF THE INVENTION

Primary mediastinal large B cell lymphoma (PMBCL), known as the "third subtype" of diffuse large B cell lymphoma (DLBCL), represents 2-4% of all B cell non-Hodgkin Lymphoma. PMBCL is recognized as a distinct clinicopathological entity in the current World Health Organization classification. The pathogenic hallmarks of PMBCL include (1) activation of the JAK-STAT pathway, (2) activation of the NF-κB pathway, and (3) overexpression of specific immune checkpoint molecules, such as programmed death ligands (PDL) 1 and 2. The current classification of PMBCL from DLBCL is based on clinico-pathologic consensus. Presently the diagnosis of PMBCL relies on the integration of clinical characteristics and clinical/pathological presentation because a reliable distinction from DLBCL solely based on morphological or immunophenotypic features can be challenging for pathologists for various reasons. Reasons for the difficulty in diagnosing PMBCL include, among others, (1) that clinico-pathologic consensus is not always well instituted, and (2) gene expression profiling developed in fresh-frozen tissue is not routinely available in clinical practice.

Gene expression profiling studies provide evidence that PMBCL can be distinguished from DLBCL on a molecular level and supported a strong relationship between PMBCL and classical Hodgkin lymphoma. However, because these studies were performed using snap-frozen tissue, the molecular classification of PMBCL has not penetrated into clinical practice.

Therefore, there is an unmet need for a gene expression-based molecular classifier using formalin-fixed, paraffin-embedded (FFPE) samples, with the ability to distinguish PMBCL from DLBCL. There is also an unmet need for additional methods of classifying DLBCL subtype tumors. The present invention provides such methods.

BRIEF SUMMARY OF THE INVENTION

In an embodiment, the present invention provides a method for classifying the lymphoma type of a sample, which method comprises providing a formalin-fixed and paraffin-embedded (FFPE) lymphoma sample from the subject, isolating RNA from the sample, obtaining gene expression data from the RNA, wherein the gene expression data comprises signal values that represent expression levels for each gene of Table 1, and determining a predictor score from the gene expression data, wherein the tumor predictors score is calculated by $$S = \sum_{k=1}^{58} a_i x_i,$$

wherein $a_i$ is the model coefficient value for gene i, as listed in Table 1, column D for determining whether the sample is PMBCL or DLBCL and as listed in Table 1 column E for determining whether a sample is ABC DLBCL or GCB DLBCL, and $x_i$ is the $\log_e$ transformed expression signal value for gene i; and when the coefficient values in column D of Table 1 are used, classifying the lymphoma as DLBCL when S is less than −57.95, PMBCL when S is greater than −23.57, or uncertain DLBCL/PMBCL when S is between −57.95 and −23.57; and when the coefficient values in column E are used, classifying the lymphoma as GCB DLBCL when S is less than 798.5, ABC DLBCL when S is greater than 1324.5, or uncertain ABC/GCB DLBCL when S is between 798.5 and 1324.5.

DETAILED DESCRIPTION OF THE INVENTION

Figure 1:
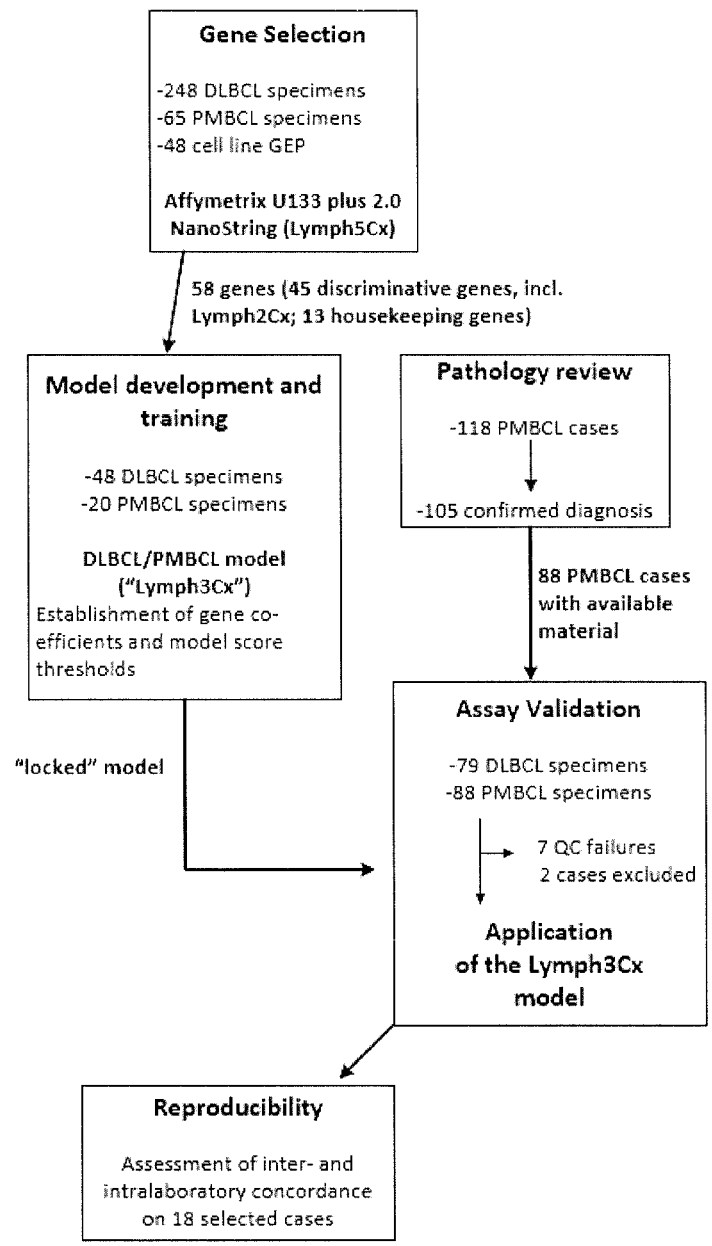
FIG. 1 presents a schematic overview of the studies described in the Example.

In an embodiment, the present invention provides a method for classifying the lymphoma type of a sample, which method comprises providing a formalin-fixed and paraffin-embedded (FFPE) lymphoma sample from the subject, isolating RNA from the sample, obtaining gene expression data from the RNA, wherein the gene expression data comprises signal values that represent expression levels for each gene of Table 1, and determining a tumor predictor score from the gene expression data, wherein the tumor predictors score is calculated by $$S = \sum_{k=1}^{58} a_i x_i,$$

wherein $a_i$ is the model coefficient value for gene i, as listed in Table 1, column D for determining whether the sample is PMBCL or DLBCL and as listed in Table 1 column E for determining whether a sample is ABC DLBCL or GCB DLBCL, and $x_i$ is the $\log_e$ transformed expression signal value for gene i; and when the coefficient values in column D of Table 1 are used, classifying the lymphoma as DLBCL when S is less than −57.95, PMBCL when S is greater than −23.57, or uncertain DLBCL/PMBCL when S is between −57.95 and −23.57; and when the coefficient values in column E are used, classifying the lymphoma as GCB DLBCL when S is less than 798.5, ABC DLBCL when S is greater than 1324.5, or uncertain ABC/GCB DLBCL when S is between 798.5 and 1324.5.

In an embodiment, the method further comprises determining the probability that the sample is PMBCL or ABC DLBCL, wherein the probability is determined by
(a) determining the probability that the sample is PMBCL by calculating the probability score of $$P(PMBCL) = \frac{\varphi(S_{PMBCL/DLBCL}; \mu_{PMBCL}, \sigma_{PMBCL})}{\varphi(S_{PMBCL/DLBCL}; \mu_{PMBCL}, \sigma_{PMBCL}) + \varphi(S_{PMBCL/DLBCL}; \mu_{PMBCL}, \sigma_{PMBCL})},$$

wherein $S_{PMBCL/DLBCL}$ is the tumor predictor score; $\mu_{PMBCL}$, $\mu_{DLBCL}$ represent the mean and standard deviations of the PMBCL and DLBCL subtypes as indicated in Table 2 provided herein;
(b) determining the probability that the sample is ABC DLBCL by calculating the probability score of $$P(ABC) = \frac{\varphi(S_{ABC/GCB}; \mu_{ABC}, \sigma_{ABC})}{\varphi(S_{ABC/GCB}; \mu_{ABC}, \sigma_{ABC}) + \varphi(S_{ABC/GCB}; \mu_{GCB}, \sigma_{GCB})},$$

wherein $S_{ABC/GCB}$ is the tumor predictor score; $\mu_{ABC}$, $\mu_{GCB}$ and $\sigma_{ABC}$, $\sigma_{GCB}$ represent the mean and standard deviations of the ABC and GCB subtypes as indicated in Table 2 herein; and
wherein $\varphi(x; \mu, \sigma)$ is the standard normal density calculated by $$\varphi(x; \mu, \sigma) = \frac{1}{\sqrt{2\pi\sigma^2}} \exp\left(-\frac{(x-\mu)^2}{2\sigma^2}\right).$$

In an embodiment, a score of P(PMBCL)≥0.9 indicates that the sample is PMBCL, regardless of the P(ABC) score. In an embodiment, a score of P(PMBCL)≤0.1 and a score of P(ABC)≤0.1 indicates that the tumor is GCB DLBCL. In an embodiment, wherein a score of P(PMBCL)≤0.1 and a score of P(ABC)≥0.9 indicates that the tumor is ABC DLBCL. In an embodiment, a score of P(PMBCL)≤0.1 and a score of P(ABC) greater than 0.1 and less than 0.9 indicates that the tumor is an unclassified DLBCL.

In an embodiment, the method encompasses genes which have a coefficient of zero. In an embodiment, the equation $$S = \sum_{k=1}^{58} a_i x_i,$$

may be utilized for determining a tumor predictor score for a sample, taking into account genes having a coefficient of zero when classifying PMBCL v. DLBCL and GCB DLBCL v. ABC DLBCL. In an embodiment the genes with a coefficient of zero need not be taken into account in the equation.

In an embodiment, the RNA gene expression data is obtained using a NanoString Technologies® nCounter® assay.

The inventive method comprises isolating sufficient RNA from a human subject, e.g., from a sample from a subject, such as from fresh tissue, a snap-frozen sample from a subject, or a formalin-fixed and paraffin-embedded (FFPE) sample from a subject. The sample may be a biopsy sample. As understood by one of ordinary skill in the art, the phrase "a snap-frozen sample from a subject" means that a sample is first taken from a subject and afterwards snap-frozen, and the phrase "obtaining or providing a formalin-fixed and paraffin-embedded (FFPE) sample from the subject" means that a sample is first taken from a subject and afterwards fixed with formalin and embedded in paraffin.

The gene expression product, e.g., the main mRNA species, is RNA, for example, total cellular mRNA. The RNA gene expression product may be obtained from the subject in any suitable manner. For example, one or more samples may be obtained from a patient that has been diagnosed as having a non-Hodgkin lymphoma, and the samples can be formalin-fixed and paraffin-embedded using protocols that are known in the art or are commercially available (see, e.g., Keiman, J. (ed.), *Histological and Histochemical Methods: Theory and Practice,* 4th edition, Cold Spring Harbor Laboratory Press (2008), incorporated herein by reference). The RNA can be extracted from an FFPE sample using methods that are known in the art or are commercially available (see, e.g., Huang et al., Cancer Epidemiol Biomarkers Prev., 19: 973-977 (2010), incorporated herein by reference; QIAGEN AIIPREP DNA/RNA FFPE Kit (Qiagen, Venlo, Netherlands)). The digital gene expression profile may be obtained from archived FFPE tissue.

The inventive method further comprises obtaining gene expression data from the isolated RNA, wherein the gene expression data comprises data for genes in a gene expression signature. The phrase "gene expression data" as used herein refers to information regarding the relative or absolute level of expression of RNA species. "Gene expression data" may be acquired for an individual cell, or for a group of cells such as a tumor or biopsy sample.

Any effective method of quantifying the expression of at least one gene, gene set, or group of gene sets may be used to acquire gene expression data for use in the invention. For example, gene expression data may be measured or estimated using one or more microarrays, where, e.g., the microarrays produce a signal value for each gene and the signal values of all genes in a gene expression signature may comprise the gene expression data. See, for example, the methods as described in the Example below.

Nucleic acid microarrays generally comprise nucleic acid probes derived from individual genes and placed in an ordered array on a support. This support may be, for example, a glass slide, a nylon membrane, or a silicon wafer. Gene expression patterns in a sample are obtained by hybridizing the microarray with the RNA gene expression product from the sample. The RNA gene expression product from a sample is labeled with a radioactive, fluorescent, or other label to allow for detection. Following hybridization, the microarray is washed, and hybridization of RNA gene expression product to each nucleic acid probe on the microarray is detected and quantified using a detection device such as a phosphoimager or scanning confocal microscope.

The microarray may be a cDNA microarray or an oligonucleotide microarray. cDNA arrays consist of hundreds or thousands of cDNA probes immobilized on a solid support, and are described in detail in, e.g., Southern et al., *Genomics*, 13: 1008-1017 (1992); Southern et al., *Nucl. Acids. Res.*, 22: 1368-1373 (1994); Gress et al., *Oncogene*, 13: 1819-1830 (1996); Pietu et al., *Genome Res.*, 6: 492-503 (1996); Schena et al., *Science*, 270: 467-470 (1995); DeRisi et al., *Nat. Genet.*, 14: 457-460 (1996); Schena et al., *Proc. Natl. Acad. Sci. USA*, 93: 10614-10619 (1996); Shalon et al., *Genome Res.*, 6: 639-645 (1996); DeRisi et al., *Science*, 278: 680-686 (1997); Heller et al., *Proc. Natl. Acad. Sci. USA*, 94: 2150-2155 (1997); and Lashkari et al., *Proc. Natl. Acad. Sci. USA*, 94: 13057-13062 (1997), each incorporated herein by reference. Oligonucleotide arrays differ from cDNA arrays in that the probes are 20- to 25-mer oligonucleotides. Oligonucleotide arrays are generally produced by in situ oligonucleotide synthesis in conjunction with photolithographic masking techniques (see, e.g., Pease et al., *Proc. Natl. Acad. Sci. USA*, 91: 5022-5026 (1994); Lipshutz et al., *Biotechniques*, 19: 442-447 (1995); Chee et al., *Science*, 274: 610-14 (1996); Lockhart et al., *Nat. Biotechnol.*, 14: 1675-1680 (1996); and Wodicka et al., *Nat. Biotechnol.*, 15: 1359-1367 (1997), each incorporated herein by reference). The solid support for oligonucleotide arrays is typically a glass or silicon surface.

Methods and techniques applicable to array synthesis and use have been described in, for example, U.S. Pat. Nos. 5,143,854, 5,242,974, 5,252,743, 5,324,633, 5,384,261, 5,424,186, 5,445,934, 5,451,683, 5,482,867, 5,491,074, 5,527,681, 5,550,215, 5,571,639, 5,578,832, 5,593,839, 5,599,695, 5,624,711, 5,631,734, 5,795,716, 5,831,070, 5,837,832, 5,856,101, 5,858,659, 5,936,324, 5,968,740, 5,974,164, 5,981,185, 5,981,956, 6,025,601, 6,033,860, 6,040,193, 6,090,555, and 6,410,229, and U.S. Patent Application Publication 2003/0104411, each incorporated herein by reference. Techniques for the synthesis of microarrays using mechanical synthesis methods are described in, for example, U.S. Pat. Nos. 5,384,261 and 6,040,193, each incorporated herein by reference. Microarrays may be nucleic acids on beads, gels, polymeric surfaces, fibers such as fiber optics, glass or any other appropriate substrate (see, e.g., U.S. Pat. Nos. 5,708,153, 5,770,358, 5,789,162, 5,800,992, and 6,040,193, each incorporated herein by reference).

Microarrays may be packaged in such a manner as to allow for diagnostic use, or they may be an all-inclusive device (see, e.g., U.S. Pat. Nos. 5,856,174 and 5,922,591, each incorporated herein by reference). Microarrays directed to a variety of purposes are commercially available from, e.g., Affymetrix (Affymetrix, Santa Clara, Calif., USA).

In an embodiment, the signal value comprises digital counts. Gene expression data can be obtained and analyzed using a variety of digital methods known in the art, such as, for example, serial analysis of gene expression (SAGE) (see, e.g., Velculescu et al., *Science*, 270(5235): 484-487 (1995)), SuperSAGE (see e.g., Matsumura et al., *Proc. Natl. Acad. Sci. USA*, 100 (26): 15718-15723 (2003)), digital northern analysis (see, e.g., Cao et al., *Breast Cancer Research*, 10: R91 (2008)), and RNA-seq (see, e.g., Mortazavi et al. *Nat Methods*, 5(7):621-628 (2008)), each article incorporated herein by reference. In an embodiment, the RNA gene expression data is obtained using a NanoString Technologies® nCounter® assay available from NanoString Technologies®, Inc. (Seattle, Wash., USA)

The NanoString platform is used for subtyping lymphomas (see e.g., Scott et al., *J. Clin. Oncol.* 31(6): 692-700 (2013), Scott et al., *Blood* 123(8): 1214-1217 (2014), Scott and Mottok et al., *J. Clin. Oncol.* 33(26): 2848-2856 (2015), Kridel and Mottok et al., *Blood* 126(18): 21118-2127 (2015), Scott and Abrisqueta et al., *J. Clin. Oncol.* 35(15): 1668-1677, Rosenwald et al., *J. Exper. Med.* 198(6): 851-862 (2003), and Savage et al., *Blood* 102(12): 3871-3879 (2003), each incorporated herein by reference.

The nCounter® assay can detect the expression of up to 800 genes in a single reaction with high sensitivity and linearity across a broad range of expression levels. The nCounter® assay is based on direct digital detection of mRNA molecules of interest using target-specific, color-coded probe pairs, and does not require the conversion of mRNA to cDNA by reverse transcription or the amplification of the resulting cDNA by PCR. Each target gene of interest is detected using a pair of reporter and capture probes carrying 35- to 50-nucleotide target-specific sequences. In addition, each reporter probe carries a unique color code at the 5' end that enables the molecular barcoding of the genes of interest, while the capture probes all carry a biotin label at the 3' end that provides a molecular handle for attachment of target genes to facilitate downstream digital detection. After solution-phase hybridization between target mRNA and reporter-capture probe pairs, excess probes are removed and the probe/target complexes are aligned and immobilized in an nCounter® cartridge, which is then placed in a digital analyzer for image acquisition and data processing. Hundreds of thousands of color codes designating mRNA targets of interest are directly imaged on the surface of the cartridge. The expression level of a gene is measured by counting the number of times the color-coded barcode for that gene is detected, and the barcode counts are then tabulated. NanoString Technologies® technology and analysis of digital gene expression data is described in detail in, e.g., Kulkarni, M. M., "Digital Multiplexed Gene Expression Analysis Using the NanoString Technologies® nCounter® System," *Current Protocols in Molecular Biology.* 94: 25B.10.1-25B.10.17 (2011), incorporated herein by reference; Geiss et al., *Nature Biotechnology,* 26: 317-325 (2008), incorporated herein by reference; and U.S. Pat. No. 7,919,237, incorporated herein by reference.

The term "gene expression signature" as used herein refers to a group of coordinately expressed genes. The genes making up a particular signature may be expressed in a specific cell lineage, stage of differentiation, or during a particular biological response. The genes may reflect biological aspects of the tumors in which they are expressed, such as the cell of origin of the cancer, the nature of the non-malignant cells in the sample, and the oncogenic mechanisms responsible for the cancer (see, e.g., Shaffer et al., *Immunity,* 15: 375-385 (2001), incorporated herein by reference). Examples of gene expression signatures include lymph node (see Shaffer et al., supra), proliferation (see, e.g., Rosenwald et al., *New Engl. J. Med.,* 346: 1937-1947 (2002), incorporated herein by reference), MHC class II, ABC DLBCL high, B-cell differentiation, T-cell, macrophage, immune response-1, immune response-2, and germinal center B cell.

The 58 genes of a gene expression signature of the present invention are shown in Table 1 with their respective coefficient values. When gene expression is detected using RNA, the sequences detected are the RNA sequences of the DNA target sequences, where the DNA sequences have thymine replaced with uracil.

TABLE 1

| | A<br>Gene Symbol | B<br>Accession | C<br>Gene Type | D<br>PMBCL/DLBCL Coefficient | E<br>ABC/GCB Coefficient | Gene Target Sequence |
|---|---|---|---|---|---|---|
| 1 | ASB13 | NM_024701.3 | GCB gene | 0 | −66.35 | GGACACGTAGGCGGTACCACTAAGGTTTTGGTAATGAGC CATTCAAACCGACAGCAGTGTGAAGGTGTGTCAAGGTGT ATATTCTCGTGGCTCGGCATTC (SEQ ID NO: 1) |
| 2 | AUH | NM_001698.2 | PMBCL gene | 3.16 | 0 | GGTGGTCTTGAACTGGCTTTAGCCTGTCTGATATACGAGTAG CAGCTTCCTCTGCAAAAATGGGCCTGGTTGAAACAAAAT TGGCCATTATTCCTGGTGGAG (SEQ ID NO: 2) |
| 3 | BANK1 | NM_001083907.1 | DLBCL gene | −0.8 | 0 | GGCAAATGAAATGGAAGGGAAGGAAAACAGAATGGAT CAGGCAGGAGAGACCAAACACAGCCCACTAGAGGTTGGCA GTGAGAGTTCTGAAGACCAGTAT (SEQ ID NO: 3) |
| 4 | BATF3 | NM_018664.2 | PMBCL gene | 2.44 | 0 | CTGTGTTATGCAGAGCCATTTCCTCTAGAATTTGGATAA TAAAGATGCTTATTGTCTCCCTTCTCCAGTTCTGGGAA TTTACAGGCACAATACACTT (SEQ ID NO: 4) |
| 5 | BTG2 | NM_006763.2 | DLBCL gene | −2.23 | 0 | TGCTCTCCTTGGGATGATGCTGGCTAGTCAGCCTTGCAT GTATTCCTTGGCGAATGGAGAGTGCCCCATGTTCTGCA AGACTACTTGGTATTCTTGT (SEQ ID NO: 5) |
| 6 | CARD11 | NM_032415.2 | DLBCL gene | −3.12 | 0 | TTGAAAATCGGCCCAAGAAGGAGCAGGTTCTGAACTGG AGCGGGAGAATGAAATGCTGAAGACTGAAGAACCAGGAG CTGCAGTTCCATCATCCAGGCCGG (SEQ ID NO: 6) |
| 7 | CCDC50 | NM_174908.3 | ABC Gene | 0 | 40.54 | AAACACTTTCCAGAGTTCCCTGCAACCCGTGCTTATGCAG ATAGTTACTATTATGAAGATGGAGGAATGAAGCCAAGAG TGATGAAAGAAGCTGTATCTA (SEQ ID NO: 7) |
| 8 | CCL17 | NM_002987.2 | PMBCL gene | 0.98 | 0 | GCCTGGAGTACTTCAAGGGAGCCATTCCCCTTAGAAAGC TGAAGACGTGGTACCAGACATCTGAAGACTGCTCCAGGG ATGCCATCGTTTTTGTAACTGT (SEQ ID NO: 8) |
| 9 | CREB3L2 | NM_194071.2 | ABC Gene | 0 | 65.79 | ATGCCTGAGGGGATCAGGCTTTCTACTCCAGGCAAACCT GCCCATCTTGTCGCTTTAGGACCTCCCACAACCTGGTT CCCCACACATCCATAGTTCT (SEQ ID NO: 9) |
| 10 | CYB5R2 | NM_016229.3 | ABC Gene | 0 | 67.72 | CCATGTCTTAGGCTTCTGTAGTAACTATGTCCAGCAAACCT TTGCAAAAATCGATAATGAATTGGTGGTCAGGGCTTAC ACCCCTGTCTCCAGTGATGAT (SEQ ID NO: 10) |
| 11 | DNAJB12 | NM_017626.4 | Housekeeping | −2.97 | −4.14 | TTTCTTCCATGTTTTAGAAAATGAGGCTGTTTGGGAAG GTACCCTGGTGATGTTTTGCTAGACATTAGCTGTAGCTG ACAGCATAAGGAGAGTCGCA (SEQ ID NO: 11) |
| 12 | FAM159A | NM_001042693.1 | DLBCL gene | −1.78 | 0 | ACAGCTACATGTGGTGCTCAGCATTGGCGCGCTCATAGG CCTGTCCGTAGCAGCAGTGGTTCTTCTCGCCTTCATTGTT ACCGCCTGTCTGTCTCTGCTA (SEQ ID NO: 12) |

TABLE 1-continued

| | A<br>Gene Symbol | B<br>Accession | C<br>Gene Type | D<br>PMBCL/DLBCL<br>Coefficient | E<br>ABC/GCB<br>Coefficient | Gene<br>Target Sequence |
|---|---|---|---|---|---|---|
| 13 | FSCN1 | NM_003088.2 | PMBCL gene | 1.01 | 0 | CCCTGCCCCTTGTCTGCCACGGGCGAGTCTGCACCTC TTTCTTCTGACCTCAGACGCTCTGAGCCTTATTCTCTGG AAGCGGCTAAGGACGGACGTT (SEQ ID NO: 13) |
| 14 | GIT2 | NM_057169.2 | Housekeeping | -2.97 | 0 | CAGATTTTACAGGCTGAATTATTGGCAGTATATGGAGCA GACCCAGGCACACAGGATTCTAGTGGGAAAACTCCCGTT GATTATGCAAGGCAAGGAGGGC (SEQ ID NO: 14) |
| 15 | GSK3B | NM_002093.2 | Housekeeping | -2.97 | -4.14 | ACTGATTATACCTCTAGTATAGATGTATGGTCTGCTGGCT GTGTGTTGCTGAGCTGTTACTAGGACACACCAATATTTCC AGGGGATAGTGGTGTGGATC (SEQ ID NO: 15) |
| 16 | HOMER2 | NM_004839.2 | PMBCL gene | 0.89 | 0 | TGGAAGACAAAGTGCGTTCCTTAAAGACAGACATTGAGG AGAGCAAATACCGACAGCGCCACCTGAAGGTGGAGTTGA AGAGCTTCCTGGAGGTGCTGGA (SEQ ID NO: 16) |
| 17 | IFIH1 | NM_022168.2 | PMBCL gene | 3.35 | 0 | GCTTGGGAGGAACCCTCCTCCCTTCTCTGAAAGAAAGAT GTCGAATGGGTATTCCACAGACAGAGAATTTCCGCTATCTC ATCTCGTGTTCAGGGCCAGG (SEQ ID NO: 17) |
| 18 | IK | NM_006083.3 | Housekeeping | -2.97 | -4.14 | GTCCAAATTCTTGGGTGGTGACATGGAACACACCATTTG GTGAAAGGCTTGGATTTTGCTCTTCAAAAGTACGAG CTGAGATTGCCAGCAAAGAG (SEQ ID NO: 18) |
| 19 | IL13RA1 | NM_001560.2 | PMBCL gene | 1.63 | 0 | TCTGCACTGAAGAAGTACGACATCTATGAAGCAAAC CAAGGAGGAAACCCTCCCACCTGAAGACGCGCCTGCCGTGCG GAAGAAGCCTCTCAGTGATGG (SEQ ID NO: 19) |
| 20 | IRF4 | NM_002460.1 | ABC Gene | 0 | 71.92 | GGGCACTGTTTAAAGGAAGTTCCGAGAAGGCATCGACA AGCCGGACCCTCCACCTGGAAGACGCGCCTGCCGTGCG CTTTGAACAAGAGCAATGACTT (SEQ ID NO: 20) |
| 21 | ISY1 | NM_020701.2 | Housekeeping | -2.97 | -4.14 | TCCTGGAGCCTCGGCGTCTTCTGGGCCTTGTGGAGTTTCT TGGACAGGGCCGCGGGGCT (SEQ ID NO: 21) |
| 22 | ITPKB | NM_002221.3 | GCB gene | 0 | -67.78 | GTGGCCTCCTGGCATCATTGTTATTGCCTCTGAAACAAG CCTTACTGCCTGGAGGGCTTTAGATTCCTGCTTCTCCAATG TAGTGTGGGTATCTTGTAGG (SEQ ID NO: 22) |
| 23 | LIMA1 | NM_001113547.1 | PMBCL gene | 1.8 | 0 | AACTACATCCTGAACTCGACGTCCTGAGTATAATACAA TCTTCGGTGCTTAGAGAGATCT (SEQ ID NO: 23) |
| 24 | LIMD1 | NM_014240.2 | ABC Gene | 0 | 61.92 | AAGGCAAGTCTCAGGAACCCATGAACTCAGGTACATCGCTTGC ACCTGTTTTAGCTTATTTAATGACGGGCTTTTGGAAGA GCTGCCCGCATACTGAGAGAC (SEQ ID NO: 24) |

TABLE 1-continued

| | A<br>Gene Symbol | B<br>Accession | C<br>Gene Type | D<br>PMBCL/DLBCL<br>Coefficient | E<br>ABC/GCB<br>Coefficient | Gene<br>Target Sequence |
|---|---|---|---|---|---|---|
| 25 | MAL | NM_002371.2 | PMBCL gene | 0.54 | 0 | GCCTTCGCGTCCGGGTTGGGAGTTGCTGTGTTAACCTC<br>CAACTGCTGCTGCTCTAGGGTCACCTCCTGTTTGTG<br>AAAGGGACCTTCTTGTTCG (SEQ ID NO: 25) |
| 26 | MAML3 | NM_018717.4 | GCB gene | 0 | -58.59 | TGGAAGCCATCAACAATTGCCCAGTAACATGCCACTGC<br>CTTCAGCTTCTCCTTCCAACTTGACCTGAAACCTTCT<br>TTGCCCTTGCAGAACAGTGG (SEQ ID NO: 26) |
| 27 | MME | NM_000902.2 | GCB gene | 0 | -56.55 | GGATTGTAGGTGCAAGCTGTCCAGAGAAAAGAGTCCTTG<br>TTCCAGCCCTATTCTGCCACTCCTGACAGGGTGACCTTGG<br>GTATTTGCAATATTCCTTTGG (SEQ ID NO: 27) |
| 28 | MOBKL2C | NM_145279.4 | PMBCL gene | 3.37 | 0 | TTTCTCTTACCCAGAGATGCCCATGAGCTGACATTTTACTC<br>ATCCCTCGCCTCCAAGAAGGCCTGTATTATACGTGTCCT<br>CCTGGGGGTTGGAGATGATC (SEQ ID NO: 28) |
| 29 | MST1R | NM_002447.1 | PMBCL gene | 1.69 | 0 | CCACTTTGGAGTTGTCTACCACGGAGAATACATAGACCA<br>GGCCCAGAATCGAATCCAATGTGCCATCAAGTCACTAAG<br>TCGCATCACAGAGATGCAGCAG (SEQ ID NO: 29) |
| 30 | MYBL1 | XM_034274.14 | GCB gene | 0 | -72.92 | GGCAAACCGCTGTTTATCCTCTTTGCAGACCATCCCAGAA<br>TTTGCAGAGACTCTAGAACTTATTGAATCTGATCCTGTAG<br>CATGGAGTGACGTTACCAGT (SEQ ID NO: 30) |
| 31 | NECAP2 | NM_018090.4 | PMBCL gene | 6.6 | 0 | CTCTCCCTCCTCCTCTTCTGGCTCTGTTGACAAACCGGG<br>CATGTTTGGCAGTAAATTGGCACCGTCACACTGTTTCC<br>TGGGATTCAAGTATGCAACC (SEQ ID NO: 31) |
| 32 | NFIL3 | NM_005384.2 | PMBCL gene | 2.06 | 0 | CCTTTCTTTCTCCTCCGCCGGCCCGAGAGCAGGAACACGAT<br>AACGAAGGAGGCCCAACTTCATTCAATAAGGAGCCTGAC<br>GGATTTATCCCAGACGGTAGA (SEQ ID NO: 32) |
| 33 | OPA1 | NM_130837.1 | Housekeeping | -2.97 | -4.14 | CTGAGACCATAATCCTTAAATGTAAAAGGCCCTGGACTAC<br>AGAGGATGGTGCTTGTTGACTTACCAGGTTGATTAATAC<br>TGTGACATCAGGCATGGCTCC (SEQ ID NO: 33) |
| 34 | PDCDILG2 | NM_025239.3 | PMBCL gene | 1.98 | 0 | AGGAAAATAAACACTCACATCCTAAAGGTTCCAGAAACA<br>GATGAGGTAGAGCTCACTGCCAGGCTACCAGGTTATCCT<br>CTGCCAGAAGTATCCTGGCCAA (SEQ ID NO: 34) |
| 35 | PHF23 | NM_024297.2 | Housekeeping | -2.97 | -4.14 | CTGTCTGTGTCCCGACACATAATCTCTGTCTCTTGGACCT<br>GCCACCATCACTTTCTGGGTCAGATTGGAATTGGGATGG<br>AATGGACAGTTGTCTATAA (SEQ ID NO: 35) |
| 36 | PIM2 | NM_006875.2 | ABC Gene | 0 | 71.8 | GCCATCCAGCACTGCCATTCCCGTGGAGTTGTCATCGTG<br>ACATCAAGGATGAGAACATCCTGATAGACCTACGCGTG<br>GCTGTGCCAAACTCATTGATT (SEQ ID NO: 36) |

TABLE 1-continued

| | A Gene Symbol | B Accession | C Gene Type | D PMBCL/DLBCL Coefficient | E ABC/GCB Coefficient | Gene Target Sequence |
|---|---|---|---|---|---|---|
| 37 | PRDX2 | NM_005809.4 | DLBCL gene | -1.28 | 0 | GCATGGGAAGTTTGTCCCGCTGCTGGAAGCTGGCAG TGACGACGATTAAGCCCAACGTGATGACAGCAAGGAATA TTTCCCAAACACAATTAGCT (SEQ ID NO: 37) |
| 38 | PRKCB | NM_212535.1 | DLBCL gene | -1.83 | 0 | GCATTTGGAGTCCTGCTGTGATGAAATGTTGGCTGGCAG CACCCTTTGAAGGGAGGATGAAGATGAACTCTTCCAAT CCATCATGGAACACAACGTAG (SEQ ID NO: 38) |
| 39 | PRR6 | NM_181716.2 | PMBCL gene | 1.33 | 0 | TTCATTGTTCCAGCTTCTCGCTTCAAGCTCCTGAAGGAG CTGAGCACATAACGACTTACACGTTCAATACTACAAAG CCCAGCATACCTTCTGTAAGA (SEQ ID NO: 39) |
| 40 | PTG1R | NM_000960.3 | PMBCL gene | 2.06 | 0 | CTGACATTTCAAGCTGACCCTGATCTCTGCCCTGTCTT CGGGCCACAGGAGCCAGAAAATCAGGGACATGGCTATT GGCTGCGGATGCTGGAACCTTG (SEQ ID NO: 40) |
| 41 | QSOX1 | NM_002826.4 | PMBCL gene | 2.85 | 0 | TAGGGCAGCTCAGTCCTGGCCTCTTAGCACCACCATTCCT GTTTTTCAGCTTATTTGAAGTCCTGCCTCATTCTCACTGGA GCCCTCAGTCTCTCCTGCTT (SEQ ID NO: 41) |
| 42 | R3HDM1 | NM_015361.2 | Housekeeping | -2.97 | -4.14 | CCCTGTTCCCAAGAGAATTACATTATTGACAAAAGACTC CAAGACGAGGATGCCAGTAGTACCCAGCAGAGGCGCCAG ATATTTAGAGTTAATAAAGAT (SEQ ID NO: 42) |
| 43 | RAB7L1 | NM_001135664.1 | ABC Gene | 0 | 70.45 | CATTTGAATTGTCTCCTGACTACTGTCCAGTAAGGAGGCC CATTGTCACTTAGAAAAGACACCTGGAACCCATGTGCATT TCTGCATCTCCTGATTAGC (SEQ ID NO: 43) |
| 44 | RCL1 | NM_005772.3 | PMBCL gene | 1.32 | 0 | TGGTGAATCATTTGAACTGAAGATTGTGCGACGGGGAAT GCCTCCCGGAGGAGGAGGCGAAGTTGGTTTTCTCATGTCCT GTGAGGAAGGTCTTTGAAGCCC (SEQ ID NO: 44) |
| 45 | RHOF | NM_019034.2 | PMBCL gene | 2.48 | 0 | CTGCGGCAAGACCTCGCTGCTCATGGTGTACAGCCAGGG CTCCTTCCCGGACACTACGCCCCATCGGTGTTCGAGAAG TACACGGCCAGCGTGACCGTT (SEQ ID NO: 45) |
| 46 | S1PR2 | NM_004230.2 | GCB gene | 0 | -78.74 | TCCCCCAGTGGCCTCCGGCCTTCATCGTCATCCTGTTT GGGCCATTGTGGTGGAAAACCTTCTGGTGCTCATTGCGGT GGCCCGAAACAGCAAGTTCC (SEQ ID NO: 46) |
| 47 | SERPINA9 | NM_001042518.1 | GCB gene | 0 | -61.81 | CCACTAAATCCTAGTGGGAAATGCCTGTTAACTGATG GCACATTGCTAATGCACAAGAAATAACAACACCATCCC TCTTTCTGTTCTGAGGGTGCAT (SEQ ID NO: 47) |
| 48 | SLAMF1 | NM_003037.2 | PMBCL gene | 1.18 | 0 | GTGTCTCTTGATCCATCCGAAGCAGGCCCTCCACGTTATC TAGGAGATCGCTACAAGTTTTATCTGGAGAATCTCACCCT GGGGATACGGGAAAGCAGGA (SEQ ID NO: 48) |

TABLE 1-continued

| | A<br>Gene Symbol | B<br>Accession | C<br>Gene Type | D<br>PMBCL/DLBCL<br>Coefficient | E<br>ABC/GCB<br>Coefficient | Gene<br>Target Sequence |
|---|---|---|---|---|---|---|
| 49 | SNX11 | NM_013323.2 | PMBCL gene | 2.79 | 0 | TCATTTGTATGTAGAGACCAGGAGTATCTCCTCAGGTGACC<br>AGTTTTGGGACCCGTATGTGGCAAATTCTAAGCTGCCAT<br>ATTGAACATCATCCCACTGG (SEQ ID NO: 49) |
| 50 | TFPI2 | NM_006528.2 | PMBCL gene | 1.06 | 0 | TTTAATCCAAGATACAGAACCTGTGATGCTTTCACCTATA<br>CTGGCTGTGGAGGAATGACAATAACTTTGTTAGCAGGG<br>AGGATTGCAAACGTGCATGTG (SEQ ID NO: 50) |
| 51 | TMOD1 | NM_003275.2 | PMBCL gene | 1.15 | 0 | AGATGCTCAAGGAGAACAAGGTGTTGAAGACACTGAATG<br>TGGAATCCAACTTCATTTCTGGAGCTGGGATTCTGCGCCT<br>GGTAGAAGCCCTCCCATACAA (SEQ ID NO: 51) |
| 52 | TNFRSF13B | NM_012452.2 | ABC Gene | 0 | 66.49 | TGCAAAACATTTGCAACCATCAGAGCCAGCGCACCTGT<br>GCAGCCCTTCTGCAGGTCACTCAGCTGCCCGCCAAGGAGCAA<br>GGCAAGTTCTATGACCATCTCC (SEQ ID NO: 52) |
| 53 | TRAF1 | NM_005658.3 | PMBCL gene | 1.98 | 0 | CGAGTGATGGGTCTAGGCCCTGAAACTGATGTCCTAGCA<br>ATAACCTCTTGATCCTACTCACCGAGTGTTGAGCCCAAG<br>GGGGATTTGTAGAACAAGCC (SEQ ID NO: 53) |
| 54 | TRIM56 | NM_030961.1 | Housekeeping | -2.97 | -4.14 | GTGGAGGCCGAGGACATTTTCCTGAAGGGCCAGGGTTGG<br>CAACTTTCAACATGGAGTGCCAAACTGCTAACCCGTCTT<br>CTAGTGTGTGAGAATAGGGAC (SEQ ID NO: 54) |
| 55 | UBXN4 | NM_014607.3 | Housekeeping | -2.97 | -4.14 | CATCGCAGCGGCCAAAAGGAGCGGCGCGTCTTCGTGGT<br>GTTCGTGGCAGGTGATGAACAGTCTACACAGATGGC<br>TGCAAGTTGGGAAGATGATAAA (SEQ ID NO: 55) |
| 56 | VRK3 | NM_016440.3 | Housekeeping | -2.97 | -4.14 | ACAGACAAGAGTGGGCGACAGTGGAAGCTGAAGTCCTTC<br>CAGACCAGGGACAACCAGGGCATTCTCTATGAAGCTGCA<br>CCCACCTCCACCCTTCACCTGTG (SEQ ID NO: 56) |
| 57 | WAC | NM_100486.2 | Housekeeping | -2.97 | -4.14 | CCTCTGGACTGAACCCCACATCTGCACCTCCAACATCGC<br>TTCAGCGGTCCCTGTTTCTCCTGTTCCACAGTCGCCAATA<br>CCTCCCTTACTTCAGGACCC (SEQ ID NO: 57) |
| 58 | WDR55 | NM_017706.4 | Housekeeping | -2.97 | -4.14 | CTACCTCTTCAATTGGAATGGCTTTGGGGCCACAAGTGAC<br>CGCTTTGCCCTGAGAGCTGAATTATCGACTGCATGGTTC<br>CAGTCACCGAGAGTCTGCTG (SEQ ID NO: 58) |

The above set of genes comprise the Lymph3Cx assay, which includes probe sets for 30 PMBCL/DLBCL predictive genes that were identified by being strongly differentially expressed between the PMBCL and DLBCL in U133+ data, strongly differentially expressed between the PMBCL and DLBCL in Lymph5Cx data, and differentially expressed between the DLBCL and PMBCL/cHL cell lines; 15 probes sets that had been included on the Lymph2Cx assay as being predictive of the ABC and GCB subtypes within DLBCL; probe sets for 13 housekeeping genes (including the 5 housekeeping genes from the Lymph2Cx assay) that showed strong expression and low variability in both U133+ and Lymph5Cx data and so were suitable for normalization. The data are discussed in the Example below.

In an embodiment, an equation used to determine a tumor predictor score is:

$$S = \sum_{k=1}^{58} a_i x_i,$$

wherein $a_i$ is the model coefficient value for gene i as listed in Table 1, column D for determining whether the sample is PMBCL or DLBCL and as listed in Table 1, column E for determining whether the sample is ABC DLBCL or GCB DLBCL, and $x_i$ is the $\log_e$ transformed expression signal value for gene i.

In an embodiment, the coefficients used to generate a tumor predictor score may be refined, and tumor predictor score cut-points used to produce model scores may be refined. For example, using methods as described herein with the same genes as those in Table 1, the coefficients for each gene may be determined to be different than as listed in Table 1 based on, e.g., the use of different types of sample (e.g., fresh) or use of different microarrays that provide different signal values. In an embodiment, the above methods may be incorporated into other methods, for example a Bayesian method as described in International Patent Application Publication No. WO 2015/069790, which is incorporated herein by reference.

In an embodiment, the present invention also provides a method for classifying a lymphoma according to the following tumor predictor scores (S value cut-points): (i) DLBCL when S is less than −57.95, (ii) PMBCL when S is greater than −23.57, (iii) uncertain DLBCL/PMBCL when S is between −57.95 and −23.57, (iv) GCB DLBCL when S is less than 798.5, (v) ABC DLBCL when S is greater than 1324.5, or (vi) uncertain ABC/GCB DLBCL when S is between 798.5 and 1324.5. Such an embodiment uses the equation $$S = \sum_{k=1}^{58} a_i x_i,$$

as defined above.

In an embodiment, an equation used to determine the probability score P(PMBCL) of a sample is $$P(PMBCL) = \frac{\varphi(S_{PMBCL/DLBCL}; \mu_{PMBCL}, \sigma_{PMBCL})}{\varphi(S_{PMBCL/DLBCL}; \mu_{PMBCL}, \sigma_{PMBCL}) + \varphi(S_{PMBCL/DLBCL}; \mu_{PMBCL}, \sigma_{PMBCL})},$$

wherein $S_{PMBCL/DLBCL}$ is the tumor predictor score; $\mu_{PMBCL}$, $\mu_{DLBCL}$ and $\sigma_{PMBCL}$, $\sigma_{DLBCL}$ represent the mean and standard deviations of the PMBCL and DLBCL subtypes as indicated in Table 2, herein.

In an embodiment, an equation used to determine the probability score P(ABC) of a sample is $$P(ABC) = \frac{\varphi(S_{ABC/GCB}; \mu_{ABC}, \sigma_{ABC})}{\varphi(S_{ABC/GCB}; \mu_{ABC}, \sigma_{ABC}) + \varphi(S_{ABC/GCB}; \mu_{GCB}, \sigma_{GCB})},$$

wherein $S_{ABC/GCB}$ is the tumor predictor score; $\mu_{ABC}$, $\mu_{GCB}$ and $\sigma_{ABC}$, $\sigma_{GCB}$ represent the mean and standard deviations of the ABC and GCB subtypes as indicated in Table 2; and wherein $\varphi(x; \mu, \sigma)$ is the standard normal density calculated by $$\varphi(x; \mu, \sigma) = \frac{1}{\sqrt{2\pi\sigma^2}} \exp\left(-\frac{(x-\mu)^2}{2\sigma^2}\right).$$

In an embodiment, after the P(PMBCL) and P(ABC) have been calculated for a particular sample, the sample is classified according Table 3, provided herein.

In an embodiment, the present invention entails the development of a set of nucleic acid probes that are able to measure the abundance of particular mRNA species using the NanoString Technologies® platform for the purpose of gene expression profiling of PMBCL in order to distinguish this lymphoma subtype from other subtypes of aggressive B cell lymphoma. In this embodiment, RNA is extracted from, e.g., FFPE, samples using standard commercial kits and then hybridized and detected. The resultant digital RNA counts reflect the relative abundance of mRNAs transcribed from different genes. These expression levels are then combined in statistical algorithms to create a tumor predictor score that provides a probability that a tumor is PMBCL, ABC DLBCL, or GCB DLBCL.

In an embodiment, the present invention provides a composition consisting of probes to the target sequences described herein. In another embodiment, the present invention also provides a kit comprising the probes, for example, a kit comprising components suitable for performing NanoString Technologies® nCounter® digital gene expression assays.

An "effective amount" or "an amount effective to treat" refers to a dose that is adequate to prevent or treat cancer in an individual. Amounts effective for a therapeutic or prophylactic use will depend on, for example, the stage and severity of the disease being treated, the age, weight, and general state of health of the patient, and the judgment of the prescribing physician. The size of the dose will also be determined by the active selected, method of administration, timing and frequency of administration, the existence, nature, and extent of any adverse side-effects that might accompany the administration of a particular active, and the desired physiological effect. It will be appreciated by one of skill in the art that various cancers could require prolonged treatment involving multiple administrations, perhaps using various rounds of administration.

The terms "treat," and "prevent" as well as words stemming therefrom, as used herein, do not necessarily imply 100% or complete treatment or prevention. Rather, there are varying degrees of treatment or prevention of which one of ordinary skill in the art recognizes as having a potential benefit or therapeutic effect. In this respect, the methods can provide any amount or any level of treatment or prevention of cancer in a subject. Furthermore, the treatment or prevention provided by the method can include treatment or prevention of one or more conditions or symptoms of the disease being treated or prevented. Also, for purposes herein, "prevention" can encompass delaying the onset of the disease, or a symptom or condition thereof, or recurrence of the disease.

Treatment can be with an effective amount of infusional dose-adjusted etoposide, doxorubicin, and cyclophosphamide with vincristine, prednisone, and rituximab (DA-EPOCH-R) when the classification is PMBCL or with an effective amount of rituximab, cyclophosphamide, doxorubicin, vincristine, and prednisone (R-CHOP) when the classification is DLBCL, uncertain DLBCL/PMBCL, GCB DLBCL, ABC DLBCL, or uncertain ABC/GCB DLBCL. When the classification is PMBCL, an effective amount of filgrastim can also be used.

For treatment, the first cycle of DA-EPOCH-R (dose level 1) can be administered as previously described (Wilson et al., J. Clin. Oncol., 26:2717-24 (2008), incorporated herein by reference) and shown in Table 4 (mg/m$^2$/day), with the following as exemplary: rituximab (rituxan; Genentech, South San Francisco, Calif., USA) 375 as 3-hour infusion day 1; doxorubicin (generic) 10, etoposide (generic) 50 and vincristine (generic) 0.4 (no cap) as a continuous infusion on days 1, 2, 3, 4 (96-hour total); cyclophosphamide (generic) 750 as 2-hour infusion on day 5; and prednisone (generic) 60 twice daily (120 mg/m$^2$/day) on days 1, 2, 3, 4, 5. Patients can receive filgrastim (neupogen; Amgen, Thousand Oaks, Calif., USA) 300 µg on day 6 through absolute neutrophil count (ANC)>5000 cells/µl (5.0×10$^9$ cells/1) past the nadir. Subsequent cycles can be dose adjusted every cycle based on the neutrophil nadir, which can be monitored with twice-weekly complete blood counts (Table 5). If the ANC nadir is ≥500 cells/µl (0.5×10$^9$ cells/1), the doses can be increased 20%; if the nadir ANC is <500 cells/µl (0.5×10$^9$ cells/1) the doses can be left unchanged; or if the platelet nadir is <25,000/µl (25.0×10$^9$ cells/I) the doses can be reduced 20% from those on the previous cycle (Table 6). Dose adjustments above dose level 1 can be applied to etoposide, doxorubicin and cyclophosphamide, and adjustments below dose level 1 can be applied to cyclophosphamide. Deviations from the adjustment paradigm can be made in the event of a critical illness on the previous cycle. Vincristine can be reduced 25% or 50% for grade 2 or 3 motor neuropathy, respectively, and can be reduced 50% for grade 3 sensory neuropathy. Patients with >1 extranodal site and elevated lactate dehydrogenase can receive intrathecal methotrexate 12 mg on day 1 and 5 of cycles 3-6.

TABLE 4

| | Dose mg/m$^2$/day | Treatment Days |
|---|---|---|
| Infusional Agents | | |
| Etoposide | 50 | |
| Vincristine | 0.4 (No cap) | Days 1, 2, 3, 4 |
| Doxorubicin | 10 | |
| Bolus Agents | | |
| Prednisone | 60 BID | Days 1, 2, 3, 4, 5 |
| Cyclophosphamide | 750 | Day 5 |
| Biologic Agents | | |
| Rituximab | 375 | Day 1 |
| Filgrastim | 5 (µg/kg) | Days 6 → ANC recovery |

Dose-Adjusted EPOCH-R Regimen. Exemplary doses for the first cycle (dose level 1) are shown. Rituximab can be infused as per manufacturers guidelines. Immediately after completion of rituximab, the infusional agents can be administered using a portable infusion pump through a central venous device. After completion of the infusions (on day 5), cyclophosphamide can be administered on the same day as per manufacturers guidelines. All treatment may be administered outpatient. Cycles can be repeated every three weeks. Patients with an ANC<1000/µl on day one of the next cycle can receive one dose of filgrastim and treated the following day if the ANC>1000/µl. Patients with platelet counts<75,000/µl can be observed for up to one week and treated when the platelets are >75,000/µl. Patients with bone marrow involvement by lymphoma can be treated on time irrespective of the ANC and platelet counts if safe. Patients can receive 6 cycles of treatment. If the tumor masses shrink>20% between the end of cycle 4 and 6, two additional cycles can be administered.

TABLE 5

Dose adjustments above level 1 apply to etoposide, doxorubicin and cyclophosphamide
Dose adjustments below level 1 apply to cyclophosphamide only.
Measurement of ANC nadir based on twice-weekly complete blood counts.
These drug doses are based on previous cycle ANC nadir as follows:
If Nadir ANC ≥500/µl: ↑ 1 dose level above last cycle
If Nadir ANC <500/µl: Same dose level as last cycle
Or
If nadir platelet <25,000/µl: ↓1 dose level below last cycle.

Pharmacodynamic Dose-Adjustment Paradigm. Dose adjustment above level 1 can apply to etoposide, doxorubicin and cyclophosphamide, and adjustments below level 1 might only apply to cyclophosphamide (see Table 6). The pharmacodynamic dose adjustment can be based on the previous cycle absolute neutrophil nadir. This can be monitored by obtaining twice weekly complete blood counts. As shown, if the ANC nadir is ≥500/µl, the doses can be increased one dose level, whereas if the ANC<500/µl, the doses can be unchanged. Reduction by one dose level can be done if the nadir platelet<$^2$5,000/µl. On rare occasions, patients may develop prolonged neutropenia<500/µl for over seven days or life threatening infections associated with organ failure or prolonged morbidity. In these cases, physicians can use their clinical judgment regarding reduction by one dose level. Doses might not be reduced for non-life threatening infections. Doses might not be reduced for neutropenia or thrombocytopenia in patients with bone marrow compromise due to marrow involvement by lymphoma unless life-threatening complications occur.

TABLE 6

| Drugs | Drug Doses per Dose Levels | | | | | | | |
|---|---|---|---|---|---|---|---|---|
| | −2 | −1 | 1 | 2 | 3 | 4 | 5 | 6 |
| Doxorubicin (mg/m²/day) | 10 | 10 | 10 | 12 | 14.4 | 17.3 | 20.7 | 24.8 |
| Etoposide (mg/m²/day) | 50 | 50 | 50 | 60 | 72 | 86.4 | 103.7 | 124.4 |
| Cyclophosphamide (mg/m²/day) | 480 | 600 | 750 | 900 | 1080 | 1296 | 1555 | 1866 |

Drug Dose Levels. Exemplary drug dose escalation for doxorubicin, etoposide and cyclophosphamide are shown for each dose level. The doses can be escalated 20% above the last cycle. The 20% dose escalation can be based on the previous doses (i.e. compounded dose escalation). Cyclophosphamide might only be adjusted when reducing below level 1.

The agents in DA-EPOCH-R are administered per manufacturer guidelines except for infusional vincristine, etoposide and doxorubicin (Wilson et al., J. Clin. Oncol., 26:2717-24 (2008) and Wilson et al., Blood, 99:2685-93 (2002), each incorporated herein by reference). The daily dose (i.e., 24 hour supply) of vincristine, doxorubicin, and etoposide can be admixed together in 0.9% Sodium Chloride Injection. The diluent volume can be based on the etoposide dose for a 24 hour treatment: If etoposide≤150 mg per 24 hours, dilute drugs in 500 mL and if etoposide>150 mg per 24 hours, dilute drugs in 1000 mL 0.9% Sodium Chloride Injection. The chemotherapy can then be administered with a suitable infusion pump via a central venous access device. Temporary PICC lines or permanent lines may be used. The bag can be exchanged daily for each of the four days to complete the 96 hour infusion. Stability studies conducted by the Pharmaceutical Development Service, Pharmacy Department, NIH Clinical Center, have demonstrated that admixtures of vincristine, doxorubicin, and etoposide in 0.9% Sodium Chloride Injection, USP at concentrations, respectively, of 1, 25, and 125 µg/mL; 1.4, 35, and 175 µg/mL; 2, 50, and 250 µg/mL; and 2.8, 70, and 350 µg/mL are stable for at least 36 hours at room temperature when protected from light (Wolfe et al., Am. J. Health Syst. Pharm., 56:985-9 (1999), incorporated by reference). Also, admixtures containing vincristine, doxorubicin, etoposide concentrations of 1.6, 40, and 200 pig/mL are stable for at least 30 hours at 32° C. Extravasation of these diluted agents should not cause local tissue damage due to their low concentrations in the diluent. Pegfilgrastim is not a recommended replacement for daily filgrastim due to its unpredictable pharmacokinetics. There may be no maximum number of dose escalations except as limited by the number of cycles.

All patients can receive the following prophylactic medications on all cycles:
  Baxtrim (sulphametoxazole and trimethoprim) DS 1 tablet TIW (equivalent if allergic)
  Omeprazole 20 mg PO QD daily (or equivalent)
  Docusate and senna 2 tablets PO BID as necessary for constipation
  Lactulose 20 gms Q6 PO as necessary for constipation.

Hepatis B surface Ag+ patients can receive anti-viral therapy daily until 8 weeks past chemotherapy completion.

See Dunleavy et al, N. Engl. J. Med., 368:1408-1416 (2013), and supplementary materials, incorporated herein by reference in its entirety, with regard to treatment.

The following includes certain aspects of the invention.

1. A method for classifying the lymphoma type of a sample, the method comprising:
  (a) providing a formalin-fixed and paraffin-embedded (FFPE) lymphoma sample from the subject;
  (b) isolating RNA from the sample;
  (c) obtaining gene expression data from the RNA, wherein the gene expression data comprises signal values that represent expression levels for each gene of Table 1; and
  (d) determining a tumor predictor score from the gene expression data, wherein the tumor predictor score is calculated by $$S = \sum_{k=1}^{58} a_i x_i,$$

wherein $a_i$ is the model coefficient value for gene i as listed in Table 1, column D for determining whether the sample is PMBCL or DLBCL and as listed in Table 1, column E for determining whether the sample is ABC DLBCL or GCB DLBCL, and $x_i$ is the $\log_2$ transformed expression signal value for gene i; and
  (e) when the coefficient values in column D of Table 1 are used, classifying the lymphoma as:
    (i) DLBCL when S is less than −57.95,
    (ii) PMBCL when S is greater than −23.57,
    (iii) uncertain DLBCL/PMBCL when S is between −57.95 and −23.57, (e') when the coefficient values in column E of Table 1 are used, classifying the lymphoma as:
    (iv) GCB DLBCL when S is less than 798.5,
    (v) ABC DLBCL when S is greater than 1324.5, or
    (vi) uncertain ABC/GCB DLBCL when S is between 798.5 and 1324.5.

2. The method of aspect 1, wherein the method further comprises determining the probability that the sample is PMBCL or ABC DLBCL, wherein the probability is determined by
  (g) determining the probability that the sample is PMBCL by calculating the probability score of $$P(PMBCL) = \frac{\varphi(S_{PMBCL/DLBCL}; \mu_{PMBCL}, \sigma_{PMBCL})}{\varphi(S_{PMBCL/DLBCL}; \mu_{PMBCL}, \sigma_{PMBCL}) + \varphi(S_{PMBCL/DLBCL}; \mu_{PMBCL}, \sigma_{PMBCL})},$$

wherein $S_{PMBCL/DLBCL}$ is the tumor predictor score; $\mu_{PMBCL}$, $\mu_{DLBCL}$ and $\sigma_{PMBCL}$, $\sigma_{DLBCL}$ represent the mean and standard deviations of the PMBCL and DLBCL subtypes as indicated in Table 2;

(h) determining the probability that the samples is ABC DLBCL by calculating the probability score of $$P(ABC) = \frac{\varphi(S_{ABC/GCB}; \mu_{ABC}, \sigma_{ABC})}{\varphi(S_{ABC/GCB}; \mu_{ABC}, \sigma_{ABC}) + \varphi(S_{ABC/GCB}; \mu_{GCB}, \sigma_{GCB})},$$

wherein $S_{ABC/GCB}$ is the tumor predictor score; $\mu_{ABC}$, $\mu_{GCB}$ and $\sigma_{ABC}$, $\sigma_{GCB}$ represent the mean and standard deviations of the ABC and GCB subtypes as indicated in Table 2; and wherein $\varphi(x; \mu, \sigma)$ is the standard normal density calculated by $$\varphi(x; \mu, \sigma) = \frac{1}{\sqrt{2\pi\sigma^2}} \exp\left(-\frac{(x-\mu)^2}{2\sigma^2}\right).$$

3. The method of aspect 2, wherein a score of P(PMBCL)≥0.9 indicates that the sample is PMBCL, regardless of the P(ABC) score.

4. The method of aspect 2, wherein a score of P(PMBCL)≤0.1 and a score of P(ABC)≤0.1 indicates that the tumor is GCB DLBCL.

5. The method of aspect 2, wherein a score of P(PMBCL)≤0.1 and a score of P(ABC)≥0.9 indicates that the tumor is ABC DLBCL.

6. The method of aspect 2, wherein a score of P(PMBCL)≤0.1 and a score of P(ABC) greater than 0.1 and less than 0.9 indicates that the tumor is an unclassified DLBCL.

7. The method of any one of aspects 1-6, wherein the RNA gene expression data is obtained using a NanoString Technologies® nCounter® assay.

8. A method of treating a human subject having lymphoma, the method comprising:

(a) obtaining a formalin-fixed and paraffin-embedded (FFPE) lymphoma sample from the subject;

(b) isolating RNA from the sample;

(c) obtaining gene expression data from the RNA, wherein the gene expression data comprises signal values that represent expression levels for each gene of Table 1;

(d) determining a tumor predictor score from the gene expression data, wherein the tumor predictor score is calculated by $$S = \sum_{k=1}^{58} a_i x_i,$$

wherein $a_i$ is the model coefficient value for gene i as listed in Table 1, column D for determining whether the sample is PMBCL or DLBCL and as listed in Table 1, column E for determining whether the sample is ABC DLBCL or GCB DLBCL, and $x_i$ is the log$_2$ transformed expression signal value for gene i;

(e) when the coefficient values in column D of Table 1 are used, classifying the lymphoma as:

(i) DLBCL when S is less than −57.95, (ii) PMBCL when S is greater than −23.57, (iii) uncertain DLBCL/PMBCL when S is between −57.95 and −23.57, (e') when the coefficient values in column E of Table 1 are used, classifying the lymphoma as:

(iv) GCB DLBCL when S is less than 798.5, (v) ABC DLBCL when S is greater than 1324.5, or (vi) uncertain ABC/GCB DLBCL when S is between 798.5 and 1324.5; and (f) treating the subject with an effective amount of DA-R-EPOCH when the classification is PMBCL or with an effective amount of R-CHOP when the classification is DLBCL, uncertain DLBCL/PMBCL, GCB DLBCL, ABC DLBCL, or uncertain ABC/GCB DLBCL.

9. The method of aspect 8, wherein the method further comprises determining the probability that the sample is PMBCL or ABC DLBCL, wherein the probability is determined by (g) determining the probability that the sample is PMBCL by calculating the probability score of $$P(PMBCL) = \frac{\varphi(S_{PMBCL/DLBCL}; \mu_{PMBCL}, \sigma_{PMBCL})}{\varphi(S_{PMBCL/DLBCL}; \mu_{PMBCL}, \sigma_{PMBCL}) + \varphi(S_{PMBCL/DLBCL}; \mu_{PMBCL}, \sigma_{PMBCL})},$$

wherein $S_{PMBCL/DLBCL}$ is the tumor predictor score; $\mu_{PMBCL}$, $\mu_{DLBCL}$ and $\sigma_{PMBCL}$, $\sigma_{DLBCL}$ represent the mean and standard deviations of the PMBCL and DLBCL subtypes as indicated in Table 2;

(h) determining the probability that the samples is ABC DLBCL by calculating the probability score of $$P(ABC) = \frac{\varphi(S_{ABC/GCB}; \mu_{ABC}, \sigma_{ABC})}{\varphi(S_{ABC/GCB}; \mu_{ABC}, \sigma_{ABC}) + \varphi(S_{ABC/GCB}; \mu_{GCB}, \sigma_{GCB})},$$

wherein $S_{ABC/GCB}$ is the tumor predictor score; $\mu_{ABC}$, $\mu_{GCB}$ and $\sigma_{ABC}$, $\sigma_{GCB}$ represent the mean and standard deviations of the ABC and GCB subtypes as indicated in Table 2; and wherein $\varphi(x; \mu, \sigma)$ is the standard normal density calculated by $$\varphi(x; \mu, \sigma) = \frac{1}{\sqrt{2\pi\sigma^2}} \exp\left(-\frac{(x-\mu)^2}{2\sigma^2}\right).$$

10. The method of aspect 9, wherein a score of P(PMBCL)≥0.9 indicates that the sample is PMBCL, regardless of the P(ABC) score.

11. The method of aspect 9, wherein a score of P(PMBCL)≤0.1 and a score of P(ABC)≤0.1 indicates that the tumor is GCB DLBCL.

12. The method of aspect 9, wherein a score of P(PMBCL)≤0.1 and a score of P(ABC)≥0.9 indicates that the tumor is ABC DLBCL.

13. The method of aspect 9, wherein a score of P(PMBCL)≤0.1 and a score of P(ABC) greater than 0.1 and less than 0.9 indicates that the tumor is an unclassified DLBCL.

14. The method of any one of aspects 8-13, wherein the RNA gene expression data is obtained using a NanoString Technologies® nCounter® assay.

It shall be noted that the preceding are merely examples of embodiments. Other exemplary embodiments are apparent from the entirety of the description herein. It will also be understood by one of ordinary skill in the art that each of these embodiments may be used in various combinations with the other embodiments provided herein.

The following example further illustrates the invention but, of course, should not be construed as in any way limiting its scope.

Example

This example demonstrates the ability of the newly developed and validated assay to distinguish a PMBCL sample from a DLBCL sample, and to distinguish between ABC DLBCL and GCB DLBCL samples based on gene expression signatures, in accordance with embodiments of the invention.

All cases included in this study were retrieved from the tissue archives of participating centers. Conventional and immunohistochemically stained slides were reviewed by at least 4 members of the Lymphoma/Leukemia Molecular Profiling Project (LLMPP) expert hematopathology panel. Information on age, sample location and clinical presentation were made available whenever possible. If 3 pathologists independently agreed, a definite diagnosis was established—all other cases were subjected to panel discussion. Pathological diagnosis is referred to as the "gold standard" for DLBCL/PMBCL classification herein. This study was conducted with approval from Institutional Review Boards according to the Declaration of Helsinki.

Details on study design, gene selection and model building are provided in FIG. 1 and below. Between the training and validation cohorts, in total 108 PMBCL and 127 DLBCL cases were studied. Following deparaffinization, RNA was extracted from up to five 10 µm formalin-fixed, paraffin-embedded (FFPE) tissue sections (tumor content≥60% of tissue area) using the Qiagen DNA/RNA FFPE Kit (Hilden, Germany) according to the manufacturer's instructions. RNA was quantified using a spectrophotometer (Nanodrop, ThermoFisher, Germany). Gene expression analysis was performed on 200 ng of RNA using a custom codeset on the NanoString platform (NanoString Technologies, Seattle, Wash., USA) at the "high sensitivity" setting on the Prep Station and 555 fields of view on second generation nCounter analyzers.

Feature/Gene Selection

To select genes with high discriminative power to distinguish between PMBCL and DLBCL, a large set of existing gene expression data, previously generated using different platforms (Lenz et al., N. Engl. J. Med., 359: 2313-2323 (2008) and Scott et al., Blood, 124: 3016-3019 (2014), both incorporated herein by reference), was interrogated.

In total 248 DLBCLs were used, all with gene expression profiling performed on fresh-frozen tissue using the Affymetrix U133 plus 2.0 microarray platform (Thermo Fisher Scientific, Waltham, Mass., USA). A subset of 79 of the cases had matching gene expression analysis performed using NanoString technology in conjunction with a customized codeset containing 814 genes (termed Lymph5Cx) on formalin-fixed, paraffin-embedded (FFPE) material (Scott et al., Blood, 124: 3016-3019 (2014)).

The dataset for PMBCL consisted of 36 gene expression profiles (GEP) generated with the Affymetrix platform and 42 targeted gene expression data derived from the Lymph5Cx assay, with 13 cases overlapping between the two platforms.

Affymetrix samples were normalized with the Affymetrix MAS5.0 algorithm and log 2-transformed. NanoString gene expression counts for a given sample were normalized by dividing the counts for each gene by the geometric mean of counts for the housekeeping genes for that sample and then multiplying them by 512. The normalized counts were then log 2-transformed. Lymph3Cx samples for which the geometric mean of the housekeeping genes was less than 60 were excluded from analysis.

In order to identify genes which were strongly predictive of subtype (i.e. DLBCL or PMBCL), a "Z-score" was calculated for each gene represented on both the Affymetrix and Lymph5Cx platform:

$$Z_i = \frac{\mu_{Pi} - \mu_{Di}}{\sqrt{\frac{n_P \sigma_{Pi}^2 + n_D \sigma_{Di}^2}{n_P + n_D}}}$$

where $\{n_P, n_D\}$ represent the number of PMBCL and DLBCL specimens available on a particular platform and $\{\mu_{Pi}, \mu_{Di}, \sigma_{Pi}^2, \sigma_{Di}^2\}$ represent their respective means and variances of the normalized signal values of gene i. The genes considered as significant were those for which both the Affymetrix and the Lymph5Cx Z-score were either greater than 1.25 or less than −1.0. In this way, the larger Affymetrix data set was used to identify potential genes, while at the same time ensuring that similar results are likely when analyzing FFPE samples. A less stringent negative cut-point than positive cut-point was used in order to avoid a large imbalance between the number of predictor genes that were characteristic of PMBCL (i.e., higher in PMBCL than DLBCL) rather than characteristic of DLBCL (i.e., higher in DLBCL than PMBCL). These cut-offs resulted in 9 DLBCL characteristic genes and 35 PMBCL characteristic genes.

Figure 2:
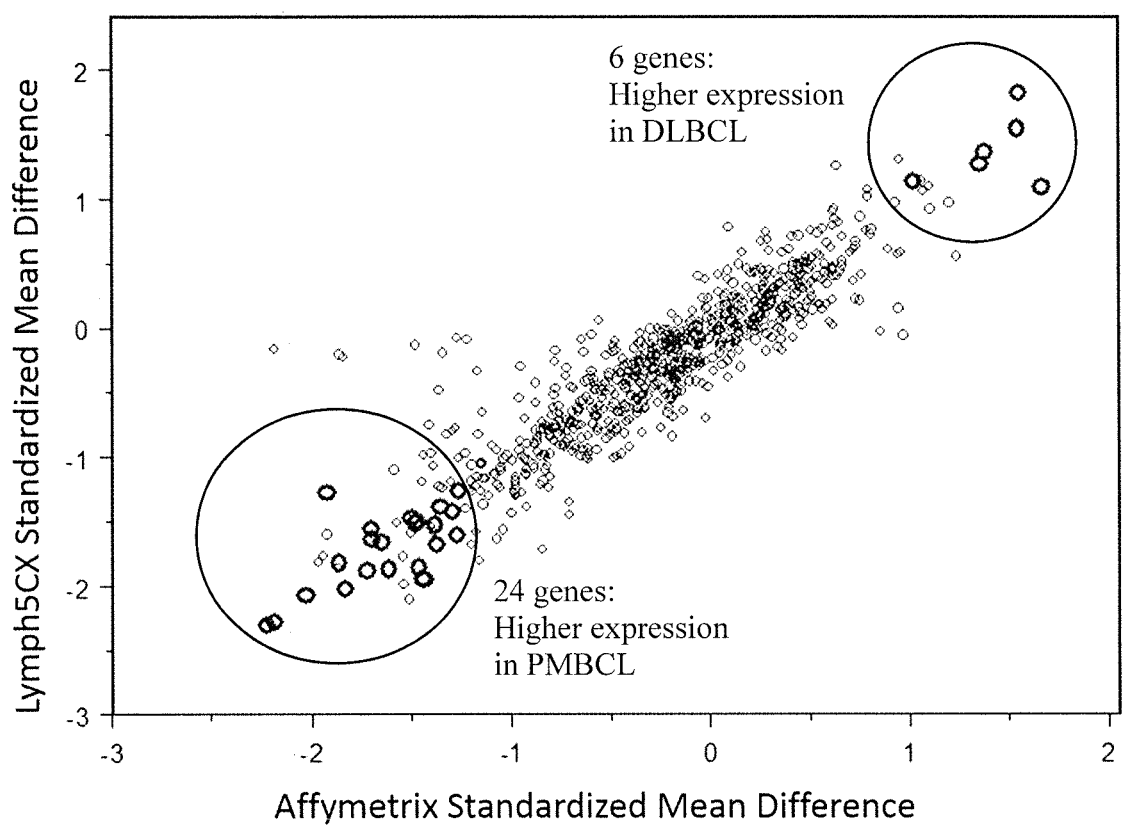
FIG. 2 is a dot plot of the genes used in selecting Nanostring probe set for the novel Lymph3Cx assay. The large circles represent the higher expressing genes in PMBCL (bottom) and DLBCL (top). The Y axis represents the Lymph5Cx standardized mean difference and the X axis represents the Affymetrix standardized mean difference. The genes with higher expression in DLBCL are CARD11, BTG2, PRKCBB, FAM159A, PRDX2, and BANK1. The genes that are higher expressed in PMBCL are MAL, HOMER2, CCL17, FSCN1, TFPI2, TMOD1, SLAMF1, RCL1, PRR6, IL13RA1, MST1R, LIMA1, TRAF1, PDCD1LG2, PTGIR, NFIL3, BATF3, RHOF, SNX11, QSOX1, AUH, IFIH1, MOBKL2C, and NECAP2.

To guard against a potential bias of selecting predominantly microenvironment/stroma-related genes, also included was GEP (generated using Affymetrix arrays) of cell lines (42 DLBCL-derived in addition to 3 PMBCL and 3 classical Hodgkin lymphoma (cHL) cell lines). A t-test between the DLBCL and the combined set of PMBCL and cHL lines was performed and any gene which did not show a significant p-value (one-sided p<0.05) in the same direction as it was observed in the patient data was excluded. In this way, the differential expression observed was due to differences in the tumor cells rather than due to infiltrating bystander cells. Fourteen genes were excluded in this step, resulting in a final list of 6 DLBCL characteristic genes and 24 PMBCL characteristic genes (FIG. 2).

Model Building and Score Formulation

The core training set of cases to build the model and define score thresholds to distinguish PMBCL from DLBCL consisted of 68 cases (48 DLBCL (19 ABC, 19 GCB, 10 unclassified DLBCL) and 20 PMBCL, according to consensus review). Data were normalized as described above. Samples with low normalizer values were excluded from further analyses. Based on the Lymph3Cx data set, a naive linear discriminant analysis score was calculated as follows:

$$S_j = \sum_{i=1}^{58} a_i x_{ij}$$

where $x_{ij}$ is the Lymph3Cx signal (log$_2$-transformed nCounter expression) for a predictive gene i on sample j, and $a_i$ is a scaling factor.

The scaling factor coefficients were calculated as follows for the DLBCL/PMBCL model:

$$a_i = \frac{\mu_{Pi} - \mu_{Di}}{(20\sigma_{Pi}^2 + 48\sigma_{Di}^2)/68}$$

$\{\mu_{Pi}, \mu_{Di}, \sigma_{Pi}^2, \sigma_{Di}^2\}$ represent the observed mean and variance of the log 2-transformed normalized counts for gene i within the PMBCL or DLBCL specimens on the Lymph3Cx platform, and the numbers 20 and 48 are derived from the number of histopathological reviewed DLBCL and PMBCL samples available on the Lymph3Cx platform. Coefficients for housekeeping genes were set to the constant value that would make the total sum of coefficients (both housekeeping and predictive genes) equal to 0. In this way, the model is automatically normalized so that a uniform fold increase or decrease of expression across all genes will have no effect on the model score.

The scaling factor coefficients for the predictive ABC/GCB genes in the Lymph3Cx ABC/GCB predictor were set equal to those in the Lymph2Cx predictor. Coefficients for housekeeping genes were set to that constant value that would make the total sum of coefficients (both housekeeping and predictive genes) equal to 0.

The values of the $a_i$ coefficients are provided in Table 1 for the DLBCL/PMBCL and ABC/GCB models.

All 38 DLBCL samples for which Lymph3Cx data was available were additionally analyzed by the Lymph2Cx array. For these samples the Lymph3Cx model score was compared to the Lymph2Cx model score and were found to be nearly identical except for shift by a constant value of 1109. Therefore, the ABC and GCB variance values were used, as in the Lymph2Cx predictor, but the ABC and GCB means were shifted by 1109 points in the Lymph3Cx predictor, as indicated in Table 2.

In order to estimate the distribution of the DLBCL vs PMBCL score within the DLBCL and PMBCL subsets score, it was important to draw from as many available cases as possible. To this end, predictor scores were generated for all 313 samples (248 DLBCL and 65 PMBCL) available.

Of the DLBCL samples, 86 were of the ABC DLBCL type, 121 were of the GCB DLBCL type and 41 were unclassified DLBCL. Of the samples, 284 samples (36 PMBCL, and all DLBCL samples) were analyzed with an Affymetrix U133+ array, 121 of the samples were analyzed with the 814 gene Lymph5Cx array (42 PMBCL, 28 ABC, 38 GCB, 13 unclassified DLBCL). Of the samples, 92 samples (13 PMBCL, 28 ABC, 38 GCB, 13 unclassified DLBCL) were analyzed with both the Affymetrix U133+ and Lymph5Cx arrays.

For each sample on each platform, a linear model score was generated based on the coefficients defined above (column D of Table 1) but using the normalized gene signal values of the particular platform. To account for platform differences, the Lymph5Cx scores were linearly normalized such that the mean and variance of the normalized Lymph5Cx model score, over the set of 68 cases for which also Lymph3Cx data was available, matched the mean and variance of the Lymph3Cx model score over the same set of cases. Similarly, the Affymetrix model score was normalized to match the normalized Lymph5Cx model score over all cases for which both Lymph5Cx and Affymetrix data was available. As a final score, the Lymph3Cx score was used for all cases for which it was available, the normalized Lymph5Cx score was used for all cases for which Lymph5Cx but not Lymph3Cx was available, and the normalized Affymetrix model score was used for cases in which Lymph5Cx/3Cx was unavailable.

In more detail, for a given sample j analyzed with the Lymph3Cx platform, a Lymph3Cx model score was calculated as $$T_j = \sum_{i=1}^{58} a_i x_{ij}$$

where $x_{ij}$ is the log transformed Lymph3Cx for gene i on sample j. Similarly, a Lymph5Cx based score for sample j was calculated as:

$$F_j = \sum_{i=1}^{58} a_i y_{ij}$$

where $y_{ij}$ is the log transformed Lymph5Cx counts for gene i on sample j. The model was then linearly adjusted so that it matches the mean and variance of the Lymph3Cx model as follows $$F'_j = \left(F_j + \operatorname*{Mean}_{k \in B}(T_k - F_k)\right) \sqrt{\frac{\operatorname*{Var}_{k \in A}(T_k)}{\operatorname*{Var}_{k \in A}(F_k)}}$$

where the mean and variance are taken over A, the set of samples for which both Lymph3Cx and Lymph5Cx data exists. The technique was then repeated for samples for which only U133+ data was available. The score was calculated as:

$$U_j = \sum_{i=1}^{58} a_i z_{ij}$$

where $z_{ij}$ is the log transformed MAS5 U133+ measure of gene expression for gene i on sample j.

$$U'_j = \left(U_j + \operatorname*{Mean}_{k \in B}(F'_k - U_k)\right) \sqrt{\frac{\operatorname*{Var}_{k \in B}(F'_k)}{\operatorname*{Var}_{k \in B}(U_k)}}$$

where the mean and variance are taken over B, the set of samples for which both Lymph5Cx and U133+ data exists. For each of the 313 samples a final model score representative was defined:

$$S_j = \begin{cases} T_j & \text{if sample } j \text{ has } Lymph3Cx \text{ data available} \\ F_j & \text{if sample } j \text{ has } Lymph5Cx \text{ data available but not } Lymph3Cx \\ U_j & \text{if sample } j \text{ has only } U133+ \text{ data available} \end{cases}$$

To account for a certain possibility of erroneous classification during the pathology review process, the final score formulation was adjusted. In modeling the relationship between model score and diagnosis, the following normal mixture model was used:

$$P(S_j|D_j=\text{DLBCL})=(1-\varepsilon_D)\varphi(S_j;\hat{\mu}_D,\hat{\sigma}_D^2)+\varepsilon_D\varphi(S_j;\hat{\mu}_P,\hat{\sigma}_P^2)$$

$$P(S_j|D_j=\text{PMBCL})=\varepsilon_P\varphi(S_j;\hat{\mu}_D,\hat{\sigma}_D^2)+(1-\varepsilon_P)\varphi(S_j;\hat{\mu}_P,\hat{\sigma}_P^2)$$

where $S_j$ is the model score for sample j; $D_j$ is the pathological diagnosis for sample j; $\varphi$ is the normal density function calculated by $$\varphi(S_j;\hat{\mu},\hat{\sigma}^2)=\frac{1}{\sqrt{2\pi\hat{\sigma}^2}}\exp\left(-\frac{(S_j-\hat{\mu})^2}{2\hat{\sigma}^2}\right)$$

and $\varepsilon_P$ and $\varepsilon_D$ are the probability of misclassification of a case as DLBCL or PMBCL; and $\hat{\mu}_D$, $\hat{\sigma}_D^2$, $\hat{\mu}_P$, $\hat{\sigma}_P^2$ are the means and variances of the model scores for cases for which the diagnosis of DLBCL or PMBCL is correct (Table 2).

The values $\varepsilon_P$, $\varepsilon_D$, $\hat{\mu}_D$, $\hat{\sigma}_D^2$, $\hat{\mu}_P$, $\hat{\sigma}_P^2$ were estimated via maximum likelihood over the 313 normalized model scores, resulting in a very low rate of pathology misclassification with $\varepsilon_P=0.033$ and $\varepsilon_D=0.0076$. The principal of maximum likelihood is used to estimate the unknown parameters by choosing those values which maximized the following expression representing the likelihood of obtaining the observed data.

$$\prod_{\substack{j\,Path\\reviewed\,as\\PMBCL}} P(S_j|D_j=DLBCL) + \prod_{\substack{j\,Path\\reviewed\,as\\DLBCL}} P(S_j|D_j=DLBCL)$$

TABLE 2

Model means and standard deviations

| Model | Subtype | Mean | Standard deviation |
|---|---|---|---|
| PMBCL/DLBCL | PMBCL | −85.60 | 24.66 |
| PMBCL/DLBCL | DLBCL | 14.42 | 31.94 |
| ABC/GCB | ABC | 2107.24 | 468.93 |
| ABC/GCB | GCB | −216.78 | 595.51 |

By estimating distributions for model scores of true DLBCL and PMBCL cases, a Bayesian algorithm was used to calculate the probability of a sample being PMBCL:

$$P(PMBCL)=\frac{\varphi(S_j;\hat{\mu}_P,\hat{\sigma}_P^2)}{\varphi(S_j;\hat{\mu}_P,\hat{\sigma}_P^2)+\varphi(S_j;\hat{\mu}_D,\hat{\sigma}_D^2)}$$

where $\varphi(S_j;\hat{\mu},\hat{\sigma}^2)$ is the standard normal density.

Since it was unknown what the composition of the target population of this assay would be, the following was assumed: a flat prior with equal a priori likelihood of a sample being of the DLBCL or PMBCL subtype.

Similarly, the probability that a sample was ABC was calculated according to:

$$P(ABC)=\frac{\varphi(S_j;\hat{\mu}_{ABC},\hat{\sigma}_{ABC})}{\varphi(S_j;\hat{\mu}_{ABC},\hat{\sigma}_{ABC}^2)+\varphi(S_j;\hat{\mu}_{GCB},\hat{\sigma}_{GCB}^2)}$$

where $\hat{\mu}_{ABC}$, $\hat{\sigma}_{ABC}^2$ and $\hat{\mu}_{GCB}$, $\hat{\sigma}_{GCB}^2$ represent the mean and standard deviations of the ABC and GCB subtypes as indicated in Table 2.

After the P(PMBCL) and P(ABC) have been calculated for a particular sample, the sample is classified according Table 3.

TABLE 3

Prediction result look-up table

| | | PMBCL/DLBCL Model result | | |
|---|---|---|---|---|
| | | P(PMBCL) ≤ 0.1 | 0.1 < P(PMBCL) < 0.9 | P(PMBCL) ≥ 0.9 |
| ABC/GCB Model Result | P(ABC) ≤ 0.1 | GCB | Unclear PMBCL/GCB | PMBCL |
| | 0.1 < P(ABC) < 0.9 | Unclassified DLBCL | Unclear PMBCL/Unclassified DLBCL | PMBCL |
| | P(ABC) ≥ 0.9 | ABC | Unclear PMBCL/ABC | PMBCL |

As a final molecular diagnosis, those specimens were designated to represent PMBCL for which P(PMBCL)≥0.9; as DLBCL for which P(PMBCL)≤0.1; and as "uncertain DLBCL/PMBCL", those cases for which 0.1<P(PMBCL)<0.9.

Also, if P(PMBCL)≥0.9 then the tumor sample will be predicted to be PMBCL regardless of the ABC/GCB predictor result. If P(PMBCL)≤0.1 and P(ABC)≤0.1 then that tumor is indicated as GCB DLBCL. If P(PMBCL)≤0.1 and P(ABC)≥0.9 then that tumor is indicated as ABC DLBCL. If (PMBCL)≤0.1 and P(ABC) is greater than 0.1 and less than 0.9, then that tumor is indicated as an unclassified DLBCL.

If the PMBCL probability falls between 0.1 and 0.9, the tumor prediction results may be unclear. For example, if 0.1<P(PMBCL)<0.9 and P(ABC)≤0.1, then the sample is indicated as unclear PMBCL/GCB. If 0.1<P(PMBCL)<0.9 and 0.1<P(ABC)<0.9, then the sample is indicated as unclear PMBCL/Unclassified DLBCL. If 0.1<P(PMBCL)<0.9 and P(ABC)≥0.9, then the sample is indicated as unclear PMBCL/GCB.

Eighteen PMBCL cases of the core training cohort were assigned to be PMBCL by the gene expression-based assay, whereas the remaining two cases were classified into the uncertain group. None of the PMBCL cases were misclassified as DLBCL. Eight DLBCL cases fell in the uncertain category and one GCB DLBCL case was classified as PMBCL by the Lymph3Cx assay. Notably, the score of this case (−15.54) was relatively close to the cut-off (−23.57). As the new assay contains the probes for DLBCL COO assignment as described previously (Scott et al., Blood, 123: 1214-1217 (2014), incorporated herein by reference), it was assessed whether the classification matches the COO as derived from gene expression profiling using snap-frozen tissue biopsies and the Affymetrix U133 plus 2.0 microarrays or the Lymph2Cx assay, respectively. A linear model score was generated using the same probe sets and coefficients as were used in the Lymph2Cx predictor (Scott et al., Blood, 123: 1214-1217 (2014); the Lymph2Cx assay is a 2-way classifier that is focused on distinguishing between two subtypes of aggressive B-cell Non-Hodgkins lymphoma: ABC-DLBCL and GCB-DLBCL; the Lymph2Cx assay does not distinguish between PMBCL and DLBCL). Of note, there was no misclassification of cases with regards to switching between the ABC and GCB classes. Nine cases changed between the unclassified category and ABC or GCB, respectively.

Validation Cases and Re-Review of Misclassified Cases

For the independent validation cohort, 118 cases diagnosed as PMBCL and collected over a period of 35 years at the Department of Pathology at the BC Cancer Agency (BCCA), Vancouver, Canada, were selected for pathology review. Five cases were re-classified (4 cases were diagnosed as DLBCL and 1 case as classical Hodgkin lymphoma). In 7 cases PMBCL was considered to be among the differential diagnoses and correlation with clinical data and presentation was recommended. In 1 case the material available for review was not sufficient to render a diagnosis, and in the remaining cases (105) the diagnosis of PMBCL was confirmed. Of these, 88 cases had sufficient material for further analysis.

For intra-laboratory comparison, RNA from 12 of the 18 biopsies selected were run a second time at BCCA, with each run performed using a different RNA aliquot and different NanoString cartridges and 6 cases were replicated at Mayo Clinic.

Results

To develop a classification assay, applicable to FFPE tissue specimens, that aims at a robust discrimination between PMBCL and DLBCL as well as the DLBCL subtypes (GCB, ABC, and unclassified, respectively), gene expression features were selected from previously published datasets (Rosenwald et al., J. Exp. Med., 198: 851-861 (2003); Lenz et al., N. Eng. J. Med., 359: 2313-2323 (2008); and Alizadeh et al., Nature, 403: 503-511 (2000); each incorporated herein by reference). The selection process, aiming at identification of genes with the highest discriminative power and good concordance between the different analytical platforms used for GEP, yielded 58 genes for subsequent assay development (Table 1). Of those, 30 genes were employed to distinguish PMBCL from DLBCL, with 24 being overexpressed in PMBCL and 6 genes showing higher expression levels in DLBCL. This approach of "balanced" gene selection was chosen to make the model less vulnerable to normalization artifacts. Additionally, 15 genes from the Lymph2Cx assay (Scott et al., Blood, 123: 1214-1217 (2014)) were included, and the remaining 13 genes were chosen as housekeeping genes, including all 5 from the Lymph2Cx assay. To train a linear regression model and establish model thresholds to distinguish PMBCL from DLBCL, a customized NanoString codeset including these 58 genes was then applied to a training cohort of 68 cases, of which 20 were diagnosed as PMBCL by consensus review and 56 were classified as DLBCL. The performance of the Lymph3Cx assay in the training cohort is shown above. The gene expression-based model, including coefficients and thresholds was "locked" and subsequently applied to the independent validation cohort comprising 167 FFPE tissue biopsies (88 PMBCL and 79 DLBCL by consensus review). None of these specimens were part of the training cohort, nor had been previously used to train the Lymph2Cx assay.

Figure 3:
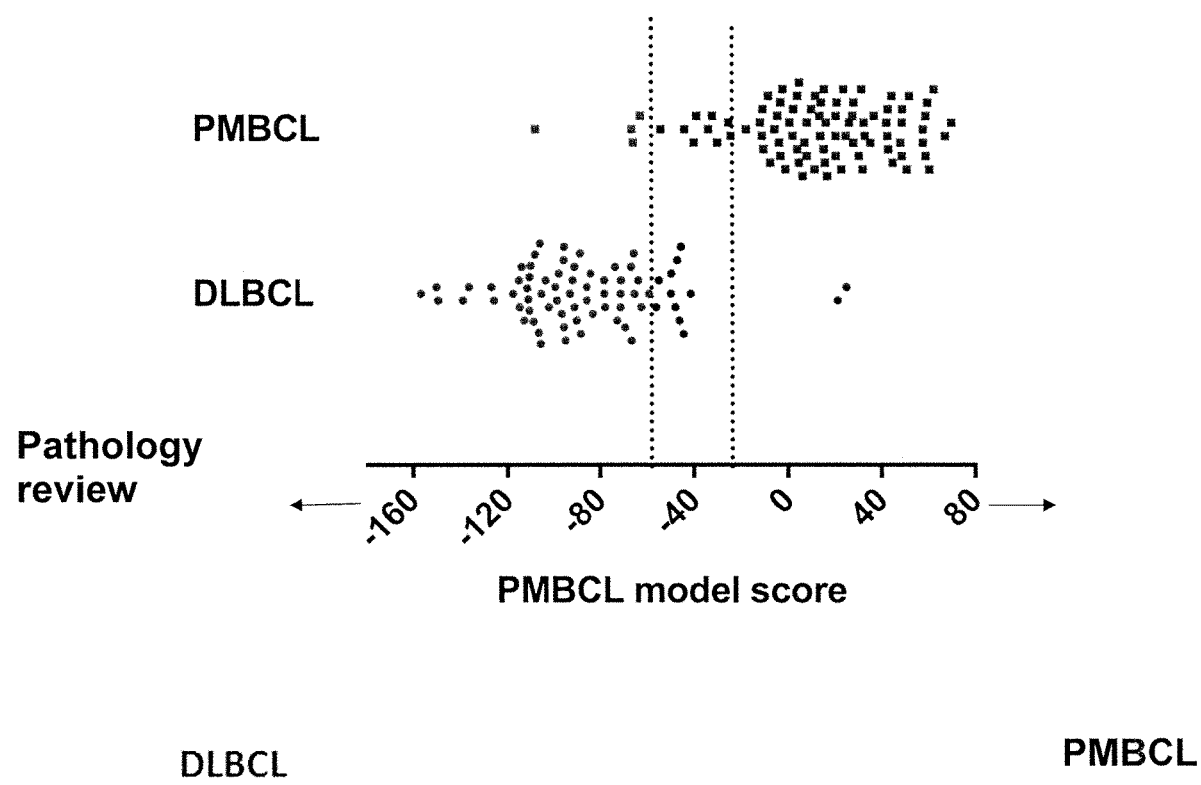
FIG. 3 shows a dot plot of the pathology review (Y axis) against the PMBCL model score (X axis) from the Lymph3Cx assay.

The assay yielded gene expression data of sufficient quality in 160/167 cases (95.8%), leaving 88 PMBCL and 70 DLBCL cases for final analysis (2 additional DLBCL cases were excluded because of a mismatch to previously analyzed frozen biopsies). Among the pathologically-defined PMBCL, 75 cases (85%) were classified as such based on Lymph3Cx. Ten percent (9 cases) were assigned to the "uncertain" category and ~5% (4 cases) showed a molecular signature of DLBCL. Of note, scores for most of the 'misclassified' PMBCLs (3/4) were close to the cut-off (FIG. 3). Among the pathologically-defined DLBCL cases, 58 (83%) were classified as DLBCL by the assay, 14% (10 cases) were "uncertain" and two cases (3%) were predicted to be PMBCL.

A pathological re-review was performed on the six misclassified cases from the validation cohort. For one DLBCL case the panel would have changed the diagnosis to PMBCL (as assigned by the assay) based on additional clinical information (young patient, mediastinal involvement), which was not available at the time of initial review. The other misclassified DLBCL case, presenting as an intraparotid lymph node enlargement with no other manifestations, was still considered to represent DLBCL. Of the 4 mis-assigned PMBCL cases, two were still felt to fit the morphological spectrum of PMBCL with typical clinical presentation, one case was deemed unclassifiable based on the available information and material for review and one case was felt to rather represent DLBCL based on the clinical information of a generalized lymphadenopathy. Of note, none of these 4 cases harbored rearrangements or copy number alteration of CIITA or the PD1 receptor ligands PDL1 and PDL2. Similar to the results obtained in the training cohort, no misclassified cases were seen with regards to DLBCL cell-of-origin (COO) subclassification. Eleven cases changed between the unclassified category and ABC or GCB, respectively.

Figure 4:
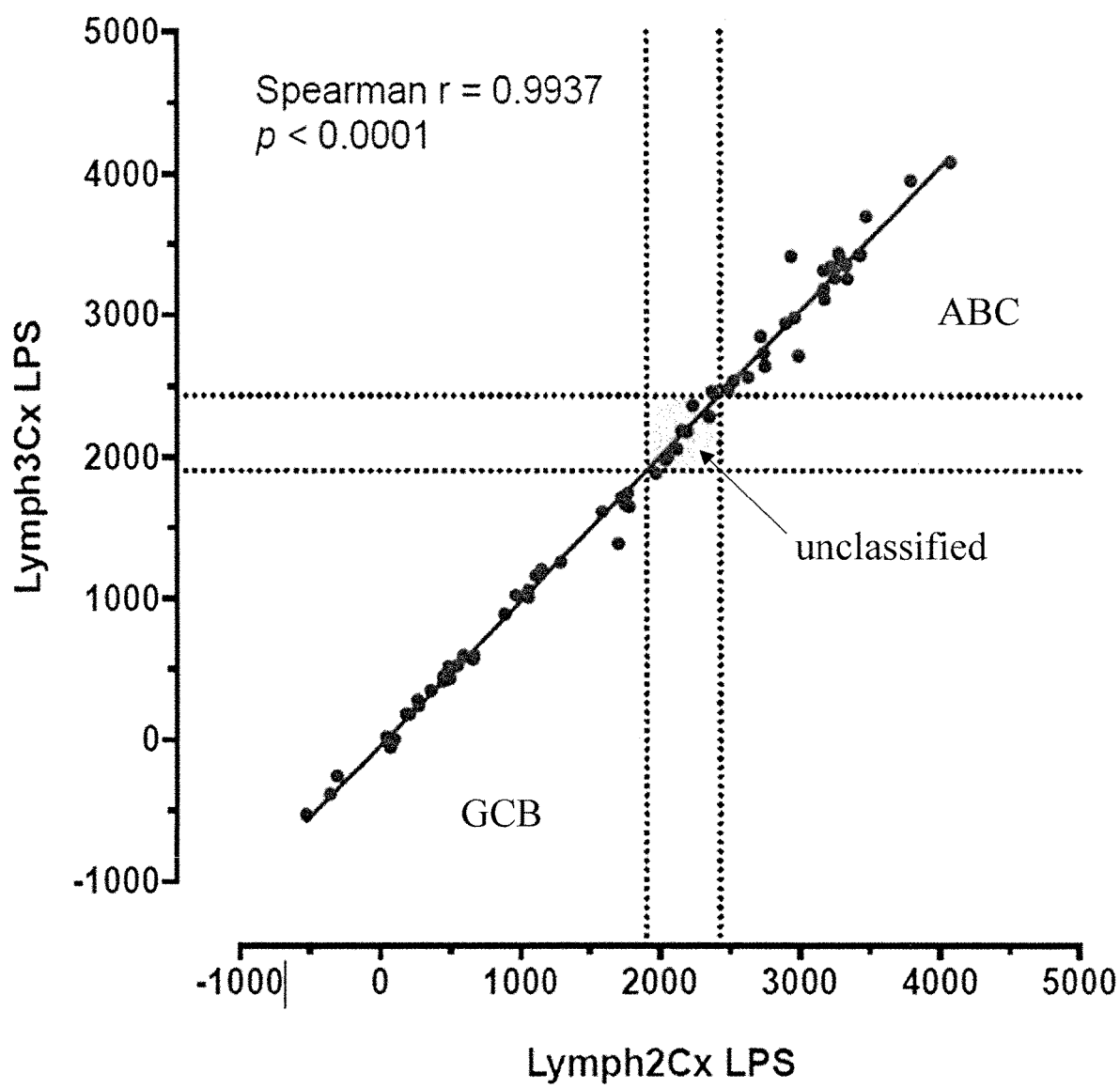
FIG. 4 is a graph showing comparison of the linear predictor scores (LPS) for 66 cases which were run using the published Lymph2Cx assay and the Lymph3Cx assay. Dotted lines represent the thresholds previously defined for COO-assignment.

For 66 cases with available COO predictions and model scores from the Lymph2Cx assay (Scott et al., Blood 123: 1214-1217 (2014) and Scott et al., J. Clin. Oncol., 33: 2848-2856 (2015), both incorporated herein by reference) the results were compared to Lymph3Cx and revealed a high correlation coefficient between both assays (Spearman r=0.9937). No classification changes were observed, demonstrating the robustness of DLBCL COO-assignment across these assays (FIG. 4).

Figure 5:
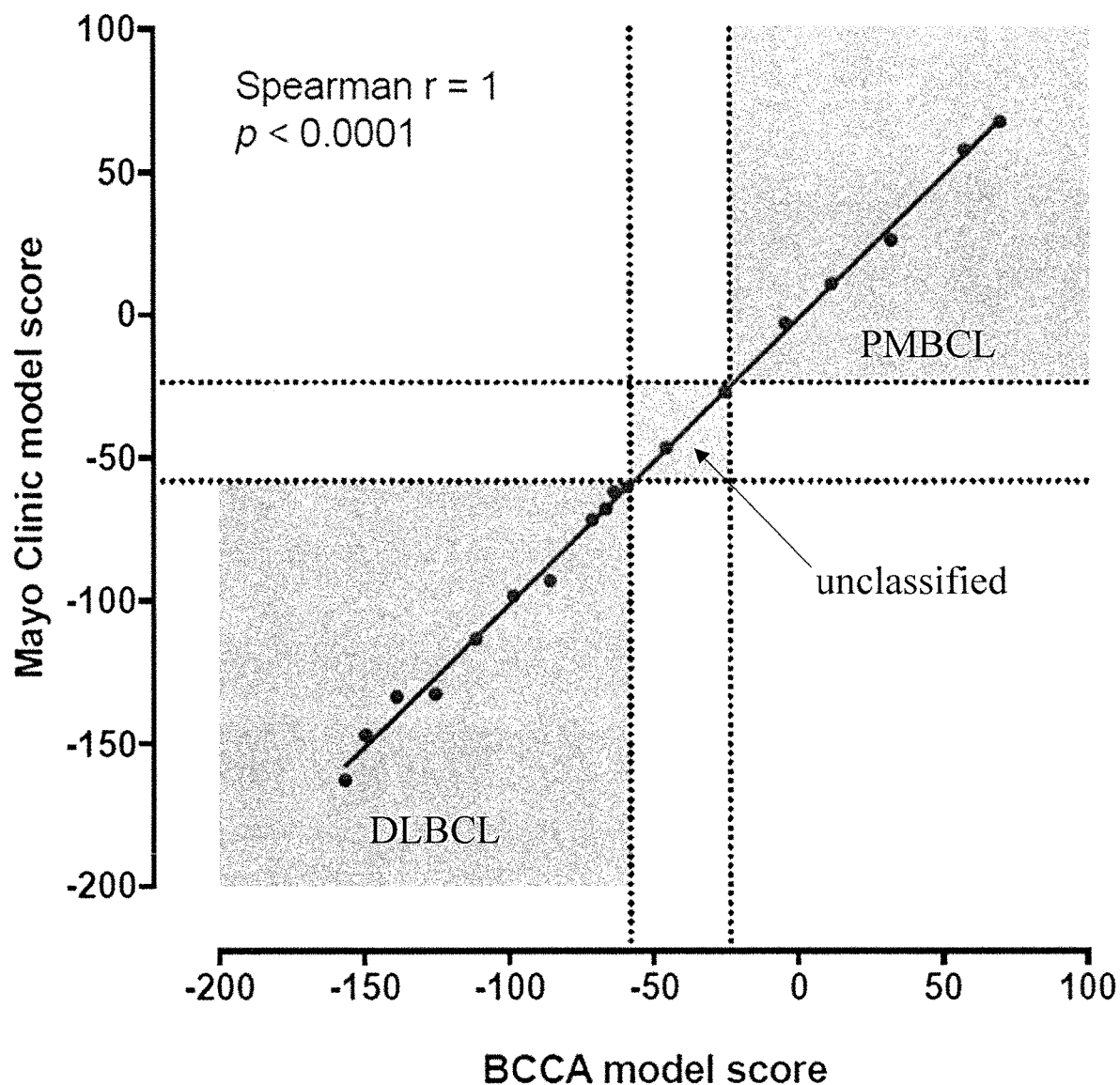
FIG. 5 is a graph showing comparison of Lymph3Cx scores for selected cases of the validation cohort from two independent laboratories (BC Cancer Agency (BCCA) and Mayo Clinic). Dotted lines represent the defined thresholds to discriminate PMBCL from DLBCL using the Lymph3Cx assay. Of note, no case changed subtype assignment between the different laboratories.

Experiments were next performed to determine intra-laboratory reproducibility and inter-laboratory concordance of the Lymph3Cx assay. Eighteen biopsies were selected on the basis that their model scores were equally distributed across the population and thus are representative of the validation cohort. For inter-laboratory comparison, separate tissue scrolls or unstained sections were distributed to an independent laboratory (Mayo Clinic, Scottsdale) where RNA was extracted and run on the Lymph3Cx assay. The concordance was excellent with Spearman $r^2=0.996$ (FIG. 5), demonstrating the robustness of the assay.

These results demonstrate that the newly developed and validated Lymph3Cx assay robustly distinguishes between PMBCL and DLBCL tumors based on gene expression signatures and shows high concordance with the pathological classification of an expert hematopathologist panel.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:
1. A method of treating a human subject having lymphoma, the method comprising:
   (a) obtaining a formalin-fixed and paraffin-embedded (FFPE) lymphoma sample from the subject;
   (b) isolating RNA from the sample;
   (c) obtaining gene expression data from the RNA, wherein the gene expression data comprises signal values that represent expression levels for each gene in the following table:

| | A<br>Gene Symbol | B<br>Accession | C<br>Gene Type | D<br>PMBCL/<br>DLBCL<br>Coefficient | E<br>ABC/<br>GCB<br>Coefficient | Gene Target Sequence |
|---|---|---|---|---|---|---|
| 1 | SymASB-13 | NM_024701.3 | GCB gene | 0 | -66.35 | GGACACGTAGGCGGTACCACTAAGGTTTTGGTAATGAGCCATTCAAACCGACAGCAGTGTGAAGGTGTGTCAAGGTGTATATTCTCGTGGCTCGGCATTC<br>(SEQ ID NO: 1) |
| 2 | AUH | NM_001698.2 | PMBCL gene | 3.16 | 0 | GGTGGTCTTGAACTGGCTTTAGCCTGTGATATACGAGTAGCAGCTTCCTCTGCAAAATGGGCCTGGTTGAAACAAAATTGGCGATTATTCCTGGTGGAG<br>(SEQ ID NO: 2) |
| 3 | BANK1 | NM_001083907.1 | DLBCL gene | -0.8 | 0 | GGCAAATGAAATGGAAGGGGAAGGAAAACAGAATGGATCAGGCATGGAGACCAAACACAGCCCACTAGAGGTTGGCAGTGAGAGTTCTGAAGACCAGTAT<br>(SEQ ID NO: 3) |
| 4 | BATF3 | NM_018664.2 | PMBCL gene | 2.44 | 0 | CTGCTGTTATGCAGAGCCATTTCCTCTAGAATTTGGATAATAAAGATGCTTATTGTCTCTCCCTTCTCCAGTTCTGGGAATTTACAGGCACAATACACTT<br>(SEQ ID NO: 4) |
| 5 | BTG2 | NM_006763.2 | DLBCL gene | -2.23 | 0 | TGCTCTCCTTGGGATGATGGCTGGCTAGTCAGCCTTGCATGTATTCCTTGGCTGAATGGGAGAGTGCCCCATGTTCTGCAAGACTACTTGGTATTCTTGT<br>(SEQ ID NO: 5) |
| 6 | CAR-D11 | NM_032415.2 | DLBCL gene | -3.12 | 0 | TTGAAAATCGGCCCAAGAAGGAGCAGGTTCTGGAACTGGAGCGGGAGAATGAAATGCTGAAGACCAAAAACCAGGAGCTGCAGTCCATCATCCAGGCCGG<br>(SEQ ID NO: 6) |
| 7 | CCD-C50 | NM_174908.3 | ABC Gene | 0 | 40.54 | AAACACTTTCCAGAGTTCCCTGCAACCCGTGCTTATGCAGATAGTTACTATTATGAAGATGGAGGAATGAAGCCAAGAGTGATGAAAGAAGCTGTATCTA<br>(SEQ ID NO: 7) |

-continued

| | A<br>Gene<br>Symbol | B<br>Accession | C<br>Gene Type | D<br>PMBCL/<br>DLBCL<br>Coefficient | E<br>ABC/<br>GCB<br>Coefficient | Gene Target Sequence |
|---|---|---|---|---|---|---|
| 8 | CCL17 | NM_002987.2 | PMBCL gene | 0.98 | 0 | GCCTGGAGTACTTCAA<br>GGGAGCCATTCCCCTT<br>AGAAAGCTGAAGACGT<br>GGTACCAGACATCTGA<br>GGACTGCTCCAGGGAT<br>GCCATCGTTTTTGTAA<br>CTGT<br>(SEQ ID NO: 8) |
| 9 | CREB-3L2 | NM_194071.2 | ABC Gene | 0 | 65.79 | ATGCCTGAGGGGATCA<br>GGCTTTTCTACTCCAG<br>GCAAACCTGCCCCATC<br>TTGTCGCTTTTAGGAC<br>CTCCCACAACCTGGTT<br>CCCCACACATCCATAG<br>TTCT<br>(SEQ ID NO: 9) |
| 10 | CYB-5R2 | NM_016229.3 | ABC Gene | 0 | 67.72 | CCATGTCTTAGGGCTT<br>CCTGTAGGTAACTATG<br>TCCAGCTCTTGGCAAA<br>AATCGATAATGAATTG<br>GTGGTCAGGGCTTACA<br>CCCCTGTCTCCAGTGA<br>TGAT<br>(SEQ ID NO: 10) |
| 11 | DNA-JB12 | NM_017626.4 | Housekeeping | -2.97 | -4.14 | TTTCTTCCATGTTTTA<br>GAAAATGAGGCCTGTT<br>TGGGGAAGGTACCCTG<br>GTGATGTTTTTGCTAG<br>ACATTAGCTGTAGCTG<br>ACAGCATAAGGAGAGT<br>CGCA<br>(SEQ ID NO: 11) |
| 12 | FAM-159A | NM_001042693.1 | DLBCL gene | -1.78 | 0 | ACAGCTACATGTGGTG<br>GCTCAGCATTGGCGCT<br>CTCATAGGCCTGTCCG<br>TAGCAGCAGTGGTTCT<br>TCTCGCCTTCATTGTT<br>ACCGCCTGTGTGCTCT<br>GCTA<br>(SEQ ID NO: 12) |
| 13 | FSCN1 | NM_003088.2 | PMBCL gene | 1.01 | 0 | CCCTGCCCTCTTGTCT<br>GCCACGGGGCGAGTCT<br>GGCACCTCTTTCTTCT<br>GACCTCAGACGGCTCT<br>GAGCCTTATTTCTCTG<br>GAAGCGGCTAAGGGAC<br>GGTT<br>(SEQ ID NO: 13) |
| 14 | GIT2 | NM_057169.2 | Housekeeping | -2.97 | -4.14 | CAGATTTTACAGGCTG<br>AATTATTGGCAGTATA<br>TGGAGCAGACCCAGGC<br>ACACAGGATTCTAGTG<br>GGAAAACTCCCGTTGA<br>TTATGCAAGGCAAGGA<br>GGGC<br>(SEQ ID NO: 14) |
| 15 | GSK3B | NM_002093.2 | Housekeeping | -2.97 | -4.14 | ACTGATTATACCTCTA<br>GTATAGATGTATGGTC<br>TGCTGGCTGTGTGTTG<br>GCTGAGCTGTTACTAG<br>GACAACCAATATTTCC<br>AGGGGATAGTGGTGTG<br>GATC<br>(SEQ ID NO: 15) |

| | A<br>Gene<br>Symbol | B<br>Accession | C<br>Gene Type | D<br>PMBCL/<br>DLBCL<br>Coefficient | E<br>ABC/<br>GCB<br>Coefficient | Gene<br>Target Sequence |
|---|---|---|---|---|---|---|
| 16 | HOMER2 | NM_004839.2 | PMBCL gene | 0.89 | 0 | TGGAAGACAAAGTGCGTTCCTTAAAGACAGACATTGAGGAGAGCAAATACCGACAGCGCCACCTGAAGGTGGAGTTGAAGAGCTTCCTGGAGGTGCTGGA<br>(SEQ ID NO: 16) |
| 17 | IFIH1 | NM_022168.2 | PMBCL gene | 3.35 | 0 | GCTTGGGAGAACCCTCTCCCTTCTCTGAGAAAGAAAGATGTCGAATGGGTATTCCACAGACGAGAATTTCCGCTATCTCATCTCGTGCTTCAGGGCCAGG<br>(SEQ ID NO: 17) |
| 18 | IK | NM_006083.3 | Housekeeping | -2.97 | -4.14 | GTCCAAATTCTTGGGTGGTGACATGGAACACACCCATTTGGTGAAAGGCTTGGATTTTGCTCTGCTTCAAAAGGTACGAGCTGAGATTGCCAGCAAAGAG<br>(SEQ ID NO: 18) |
| 19 | IL13-RA1 | NM_001560.2 | PMBCL gene | 1.63 | 0 | TCTGCACTGGAAGAAGTACGACATCTATGAGAAGCAAACCAAGGAGAAACCGACTCTGTAGTGCTGATAGAAACCTGAAGAAAGCCTCTCAGTGATGG<br>(SEQ ID NO: 19) |
| 20 | IRF4 | NM_002460.1 | ABC Gene | 0 | 71.92 | GGGCACTGTTTAAAGGAAAGTTCCGAGAAGGCATCGACAAGCCGGACCCTCCCACCTGGAAGACGCGCCTGCGGTGCGCTTTGAACAAGAGCAATGACTT<br>(SEQ ID NO: 20) |
| 21 | ISY1 | NM_020701.2 | Housekeeping | -2.97 | -4.14 | GGCAAAACATCAGTGTCTGTGGGTAGTTGGAATCTTCAGTTCCTGTGAGCGTCGGCGTCTTCTGGGCCTGTGGAGTTTCTTGGACAGGGGCCGCGGGGCT<br>(SEQ ID NO: 21) |
| 22 | ITPKB | NM_002221.3 | GCB gene | 0 | -67.78 | GTGGCCTCCTGGCATCATTTGTTATTGCCTCTGAAACAAGCCTTACTGCCTGGAGGGCTTAGATTCCTGCTTCTCCAATGTAGTGTGGGTATCTTGTAGG<br>(SEQ ID NO: 22) |
| 23 | LIMA1 | NM_001113547.1 | PMBCL gene | 1.8 | 0 | AACTACATCCTGAACTCGACGTCCTGAGGTATAATACAACAGAGCACTTTTTGAGGCAATTGAAAAACCAACCTACACTCTTCGGTGCTTAGAGAGATCT<br>(SEQ ID NO: 23) |

| | A<br>Gene<br>Symbol | B<br>Accession | C<br>Gene Type | D<br>PMBCL/<br>DLBCL<br>Coefficient | E<br>ABC/<br>GCB<br>Coefficient | Gene<br>Target Sequence |
|---|---|---|---|---|---|---|
| 24 | LIMD1 | NM_014240.2 | ABC Gene | 0 | 61.92 | AAGGCAAGTCTCAGGA<br>ACCCATGCAGGTACAT<br>CGCTTGCACCTGTTTT<br>TAGCTTATTTAATGAC<br>GGGCTTTTGGGAAGAG<br>CTGCCCGCATACTGAG<br>AGAC<br>(SEQ ID NO: 24) |
| 25 | MAL | NM_002371.2 | PMBCL gene | 0.54 | 0 | GCCTTCGCGTCCGGGT<br>TGGGAGCTTGCTGTGT<br>CTAACCTCCAACTGCT<br>GTGCTGTCTGCTAGGG<br>TCACCTCCTGTTTGTG<br>AAAGGGGACCTTCTTG<br>TTCG<br>(SEQ ID NO: 25) |
| 26 | MAML3 | NM_018717.4 | GCB gene | 0 | -58.59 | TGGAAGCCATCAACAA<br>TTTGCCCAGTAACATG<br>CCACTGCCTTCAGCTT<br>CTCCTCTTCACCAACT<br>TGACCTGAAACCTTCT<br>TTGCCCTTGCAGAACA<br>GTGG<br>(SEQ ID NO: 26) |
| 27 | MME | NM_000902.2 | GCB gene | 0 | -56.55 | GGATTGTAGGTGCAAG<br>CTGTCCAGAGAAAAGA<br>GTCCTTGTTCCAGCCC<br>TATTCTGCCACTCCTG<br>ACAGGGTGACCTTGGG<br>TATTTGCAATATTCCT<br>TTGG<br>(SEQ ID NO: 27) |
| 28 | MOBK-L2C | NM_145279.4 | PMBCL gene | 3.37 | 0 | TTCTCTTACCCAGAGA<br>TGCCCATGAGCTGACA<br>TTTTACTCATCCCTCT<br>GCCTCCAAGAAGGCCT<br>GTATTATACGTGTCCT<br>CCTGGGGGTTGGAGAT<br>GATC<br>(SEQ ID NO: 28) |
| 29 | MST1R | NM_002447.1 | PMBCL gene | 1.69 | 0 | CCACTTTGGAGTTGTC<br>TACCACGGAGAATACA<br>TAGACCAGGCCCAGAA<br>TCGAATCCAATGTGCC<br>ATCAAGTCACTAAGTC<br>GCATCACAGAGATGCA<br>GCAG<br>(SEQ ID NO: 29) |
| 30 | MYBL1 | XM_034274.14 | GCB gene | 0 | -72.92 | GGCAAACGCTGTGTTA<br>TCCTCTTTGCAGACCA<br>TCCCAGAATTTGCAGA<br>GACTCTAGAACTTATT<br>GAATCTGATCCTGTAG<br>CATGGAGTGACGTTAC<br>CAGT<br>(SEQ ID NO: 30) |
| 31 | NECAP2 | NM_018090.4 | PMBCL gene | 6.6 | 0 | CTCTCCTCTCCTCCTT<br>GTCTGGCTCTGTTGAC<br>AAACCGGGCATGTTTG<br>GCAGTAAATTGGCACC<br>GTGTCACACTGTTTCC<br>TGGGATTCAAGTATGC<br>AACC<br>(SEQ ID NO: 31) |

-continued

| | A Gene Symbol | B Accession | C Gene Type | D PMBCL/ DLBCL Coefficient | E ABC/ GCB Coefficient | Gene Target Sequence |
|---|---|---|---|---|---|---|
| 32 | NFIL3 | NM_005384.2 | PMBCL gene | 2.06 | 0 | CCTTTCTTTCTCCTCG CCGGCCCGAGAGCAGG AACACGATAACGAAGG AGGCCCAACTTCATTC AATAAGGAGCCTGACG GATTTATCCCAGACGG TAGA (SEQ ID NO: 32) |
| 33 | OPA1 | NM_130837.1 | Housekeeping | -2.97 | -4.14 | CTGAGACCATATCCTT AAATGTAAAAGGCCCT GGACTACAGAGGATGG TGCTTGTTGACTTACC AGGTGTGATTAATACT GTGACATCAGGCATGG CTCC (SEQ ID NO: 33) |
| 34 | PDCD-1LG2 | NM_025239.3 | PMBCL gene | 1.98 | 0 | AGGAAAATAAACACTC ACATCCTAAAGGTTCC AGAAACAGATGAGGTA GAGCTCACCTGCCAGG CTACAGGTTATCCTCT GGCAGAAGTATCCTGG CCAA (SEQ ID NO: 34) |
| 35 | PHF23 | NM_024297.2 | Housekeeping | -2.97 | -4.14 | CTGTCTGTGTCCCGAC ACATAATCTCTGTCTC TTGGACCTGCCACCAT CACTTTCTGGGTCAGG ATTGGAATTGGGATGG AATGGGACAGTTGTCT ATAA (SEQ ID NO: 35) |
| 36 | PIM2 | NM_006875.2 | ABC Gene | 0 | 71.8 | GCCATCCAGCACTGCC ATTCCCGTGGAGTTGT CCATCGTGACATCAAG GATGAGAACATCCTGA TAGACCTACGCCGTGG CTGTGCCAAACTCATT GATT (SEQ ID NO: 36) |
| 37 | PRDX2 | NM_005809.4 | DLBCL gene | -1.28 | 0 | GCATGGGGAAGTTTGT CCCGCTGGCTGGAAGC CTGGCAGTGACACGAT TAAGCCCAACGTGGAT GACAGCAAGGAATATT TCTCCAAACACAATTA GGCT (SEQ ID NO: 37) |
| 38 | PRKCB | NM_212535.1 | DLBCL gene | -1.83 | 0 | GCATTTGGAGTCCTGC TGTATGAAATGTTGGC TGGGCAGGCACCCTTT GAAGGGGAGGATGAAG ATGAACTCTTCCAATC CATCATGGAACACAAC GTAG (SEQ ID NO: 38) |
| 39 | PRR6 | NM_181716.2 | PMBCL gene | 1.33 | 0 | TTCATTGTTCCAGCTT CTCGCTTCAAGCTCCT GAAGGGAGCTGAGCAC ATAACGACTTACACGT TCAATACTCACAAAGC CCAGCATACCTTCTGT AAGA (SEQ ID NO: 39) |

-continued

| | A Gene Symbol | B Accession | C Gene Type | D PMBCL/DLBCL Coefficient | E ABC/GCB Coefficient | Gene Target Sequence |
|---|---|---|---|---|---|---|
| 40 | PTGIR | NM_000960.3 | PMBCL gene | 2.06 | 0 | CTGACATTTCAAGCTGACCCTGTGATCTCTGCCCTGTCTTCGGGCGACAGGAGCCAGAAAATCAGGGACATGGCTGATGGCTGCGGATGCTGGAACCTTG (SEQ ID NO: 40) |
| 41 | QSOX1 | NM_002826.4 | PMBCL gene | 2.85 | 0 | TAGGGCAGCTCAGTCCCTGGCCTCTTAGCACCACATTCCTGTTTTTCAGCTTATTTGAAGTCCTGCCTCATTCTCACTGGAGCCTCAGTCTCTCCTGCTT (SEQ ID NO: 41) |
| 42 | R3HDM1 | NM_015361.2 | Housekeeping | -2.97 | -4.14 | CCTGTGTTCCCAAGAGAATTACATTATTGACAAAGACTCCAAGACGAGGATGCCAGTAGTACCCAGCAGAGGCGCCAGATATTTAGAGTTAATAAAGAT (SEQ ID NO: 42) |
| 43 | RAB7L1 | NM_001135664.1 | ABC Gene | 0 | 70.45 | CATTTGAATTGTCTCCTGACTACTGTCCAGTAAGGAGGCCCATTGTCACTTAGAAAAGACACCTGGAACCCATGTGCATTTCTGCATCTCCTGGATTAGC (SEQ ID NO: 43) |
| 44 | RCL1 | NM_005772.3 | PMBCL gene | 1.32 | 0 | TGGTGAATCATTTGAACTGAAGATTGTGCGACGGGGAATGCCTCCCGGAGGAGGAGGCGAAGTGGTTTTCTCATGTCCTGTGAGGAAGGTCTTGAAGCCC (SEQ ID NO: 44) |
| 45 | RHOF | NM_019034.2 | PMBCL gene | 2.48 | 0 | CTGCGGCAAGACCTCGCTGCTCATGGTGTACAGCCAGGGCTCCTTCCCCGAGCACTACGCCCCATCGGTGTTCGAGAAGTACACGGCCAGCGTGACCGTT (SEQ ID NO: 45) |
| 46 | S1PR2 | NM_004230.2 | GCB gene | 0 | -78.74 | TCCCGCCAGGTGGCCTCGGCCTTCATCGTCATCCTCTGTTGCGCCATTGTGGTGGAAAACCTTCTGGTGCTCATTGCGGTGGCCCGAAACAGCAAGTTCC (SEQ ID NO: 46) |
| 47 | SERPINA9 | NM_001042518.1 | GCB gene | 0 | -61.81 | CCACTAAATCCTAGGTGGGAAATGGCCTGTTAACTGATGGCACATTGCTAATGCACAAGAAATAACAAACCACATCCCTCTTTCTGTTCTGAGGGTGCAT (SEQ ID NO: 47) |

-continued

| | A<br>Gene<br>Symbol | B<br>Accession | C<br>Gene Type | D<br>PMBCL/<br>DLBCL<br>Coefficient | E<br>ABC/<br>GCB<br>Coefficient | Gene<br>Target Sequence |
|---|---|---|---|---|---|---|
| 48 | SLAMF1 | NM_003037.2 | PMBCL gene | 1.18 | 0 | GTGTCTCTTGATCCAT<br>CCGAAGCAGGCCCTCC<br>ACGTTATCTAGGAGAT<br>CGCTACAAGTTTTATC<br>TGGAGAATCTCACCCT<br>GGGGATACGGGAAAGC<br>AGGA<br>(SEQ ID NO: 48) |
| 49 | SNX11 | NM_013323.2 | PMBCL gene | 2.79 | 0 | TCATTTGTATGTAGGA<br>CCAGGAGTATCTCCTC<br>AGGTGACCAGTTTTGG<br>GGACCCGTATGTGGCA<br>AATTCTAAGCTGCCAT<br>ATTGAACATCATCCCA<br>CTGG<br>(SEQ ID NO: 49) |
| 50 | TFPI2 | NM_006528.2 | PMBCL gene | 1.06 | 0 | TTTAATCCAAGATACA<br>GAACCTGTGATGCTTT<br>CACCTATACTGGCTGT<br>GGAGGGAATGACAATA<br>ACTTTGTTAGCAGGGA<br>GGATTGCAAACGTGCA<br>TGTG<br>(SEQ ID NO: 50) |
| 51 | TMOD1 | NM_003275.2 | PMBCL gene | 1.15 | 0 | AGATGCTCAAGGAGAA<br>CAAGGTGTTGAAGACA<br>CTGAATGTGGAATCCA<br>ACTTCATTTCTGGAGC<br>TGGGATTCTGCGCCTG<br>GTAGAAGCCCTCCCAT<br>ACAA<br>(SEQ ID NO: 51) |
| 52 | TNFRS-F13B | NM_012452.2 | ABC Gene | 0 | 66.49 | TGCAAAACCATTTGCA<br>ACCATCAGAGCCAGCG<br>CACCTGTGCAGCCTTC<br>TGCAGGTCACTCAGCT<br>GCCGCAAGGAGCAAGG<br>CAAGTTCTATGACCAT<br>CTCC<br>(SEQ ID NO: 52) |
| 53 | TRAF1 | NM_005658.3 | PMBCL gene | 1.98 | 0 | CGAGTGATGGGTCTAG<br>GCCCTGAAACTGATGT<br>CCTAGCAATAACCTCT<br>TGATCCCTACTCACCG<br>AGTGTTGAGCCCAAGG<br>GGGGATTTGTAGAACA<br>AGCC<br>(SEQ ID NO: 53) |
| 54 | TRIM56 | NM_030961.1 | Housekeeping | -2.97 | -4.14 | GTGGAGGCCGAGGACA<br>TTTTCCTGAAGGGCAG<br>GGGTTGGCAACTTTTC<br>AACATGGAGTGCCAAA<br>CTGCTAACCCGTCTTC<br>TAGTGTGTGAGAATAG<br>GGAC<br>(SEQ ID NO: 54) |
| 55 | UBXN4 | NM_014607.3 | Housekeeping | -2.97 | -4.14 | CATCGCGACGGCCAAA<br>AGGAGCGGCGCGGTCT<br>TCGTGGTGTTCGTGGC<br>AGGTGATGATGAACAG<br>TCTACACAGATGGCTG<br>CAAGTTGGGAAGATGA<br>TAAA<br>(SEQ ID NO: 55) |

-continued

| | A<br>Gene<br>Symbol | B<br>Accession | C<br>Gene Type | D<br>PMBCL/<br>DLBCL<br>Coefficient | E<br>ABC/<br>GCB<br>Coefficient | Gene Target Sequence |
|---|---|---|---|---|---|---|
| 56 | VRK3 | NM_016440.3 | Housekeeping | -2.97 | -4.14 | ACAGACAAGAGTGGGC<br>GACAGTGGAAGCTGAA<br>GTCCTTCCAGACCAGG<br>GACAACCAGGGCATTC<br>TCTATGAAGCTGCACC<br>CACCTCCACCCTCACC<br>TGTG<br>(SEQ ID NO: 56) |
| 57 | WAC | NM_<br>100486.2 | Housekeeping | -2.97 | -4.14 | CCTCTGGACTGAACCC<br><br>CACATCTGCACCTCCA<br>ACATCTGCTTCAGCGG<br>TCCCTGTTTCTCCTGT<br>TCCACAGTCGCCAATA<br>CCTCCCTTACTTCAGG<br>ACCC<br>(SEQ ID NO: 57) |
| 58 | WDR55 | NM_017706.4 | Housekeeping | -2.97 | -4.14 | CTACCTCTTCAATTGG<br>AATGGCTTTGGGGCCA<br>CAAGTGACCGCTTTGC<br>CCTGAGAGCTGAATCT<br>ATCGACTGCATGGTTC<br>CAGTCACCGAGAGTCT<br>GCTG<br>(SEQ ID NO: 58); |

(d) determining a tumor predictor score from the gene expression data, wherein the tumor predictor score is calculated by $$S = \sum_{k=1}^{58} a_i x_i,$$

wherein $a_i$ is the model coefficient value for gene i as listed in the table of (c), column D for determining whether the sample is PMBCL or DLBCL and as listed in the table of (c), column E for determining whether the sample is ABC DLBCL or GCB DLBCL,
and $x_i$ is the log$_2$ transformed expression signal value for gene i;
(e) when the coefficient values in column D of the table of (c) are used, classifying the lymphoma as:
 (i) DLBCL when S is less than −57.95,
 (ii) PMBCL when S is greater than −23.57,
 (iii) uncertain DLBCL/PMBCL when S is between −57.95 and −23.57,
(e') when the coefficient values in column E of the table of (c) are used, classifying the lymphoma as:
 (iv) GCB DLBCL when S is less than 798.5,
 (v) ABC DLBCL when S is greater than 1324.5, or
 (vi) uncertain ABC/GCB DLBCL when S is between 798.5 and 1324.5; and
(f) treating the subject with an effective amount of DA-R-EPOCH when the classification is PMBCL or with an effective amount of R-CHOP when the classification is DLBCL, uncertain DLBCL/PMBCL, GCB DLBCL, ABC DLBCL, or uncertain ABC/GCB DLBCL.

2. The method of claim 1, wherein the method further comprises determining the probability that the sample is PMBCL or ABC DLBCL, wherein the probability is determined by
 (f) determining the probability that the sample is PMBCL by calculating the probability score of $$P(PMBCL) = \frac{\varphi(S_{PMBCL/DLBCL}; \mu_{PMBCL}, \sigma_{PMBCL})}{\varphi(S_{PMBCL/DLBCL}; \mu_{PMBCL}, \sigma_{PMBCL}) + \varphi(S_{PMBCL/DLBCL}; \mu_{PMBCL}, \sigma_{PMBCL})},$$

wherein $S_{PMBCL/DLBCL}$ is the tumor predictor score; $\mu_{PMBCL}$, $\mu_{DLBCL}$ and $\sigma_{PMBCL}$, $\sigma_{DLBCL}$ represent the mean and standard deviations of the PMBCL and DLBCL subtypes as indicated in the following table:

| Model | Subtype | Mean | Standard deviation |
|---|---|---|---|
| PMBCL/DLBCL | PMBCL | -85.60 | 24.66 |
| PMBCL/DLBCL | DLBCL | 14.42 | 31.94 |
| ABC/GCB | ABC | 2107.24 | 468.93 |
| ABC/GCB | GCB | -216.78 | 595.51; |

(g) determining the probability that the samples is ABC DLBCL by calculating the probability score of $$P(ABC) = \frac{\varphi(S_{ABC/GCB}; \mu_{ABC}, \sigma_{ABC})}{\varphi(S_{ABC/GCB}; \mu_{ABC}, \sigma_{ABC}) + \varphi(S_{ABC/GCB}; \mu_{GCB}, \sigma_{GCB})},$$

wherein $S_{ABC/GCB}$ is the tumor predictor score; $\mu_{ABC}$, $\mu_{GCB}$ and $\sigma_{ABC}$, $\sigma_{GCB}$ represent the mean and standard deviations of the ABC and GCB subtypes as indicated in the table of (f); and wherein $\varphi(x; \mu, \sigma)$ is the standard normal density calculated by $$\varphi(x; \mu, \sigma) = \frac{1}{\sqrt{2\pi\sigma^2}} \exp\left(-\frac{(x-\mu)^2}{2\sigma^2}\right).$$

3. The method of claim 2, wherein a score of P(PMBCL)≥0.9 indicates that the sample is PMBCL, regardless of the P(ABC) score.

4. The method of claim 2, wherein a score of P(PMBCL)≤0.1 and a score of P(ABC)≤0.1 indicates that the tumor is GCB DLBCL.

5. The method of claim 2, wherein a score of P(PMBCL)≤0.1 and a score of P(ABC)≥0.9 indicates that the tumor is ABC DLBCL.

6. The method of claim 2, wherein a score of P(PMBCL)≤0.1 and a score of P(ABC) greater than 0.1 and less than 0.9 indicates that the tumor is an unclassified DLBCL.

7. The method of any one of claims 1-6, wherein the RNA gene expression data is obtained using an assay comprising color-coded probes.

* * * * *